(12) United States Patent
Goldstein et al.

(10) Patent No.: US 11,407,806 B2
(45) Date of Patent: Aug. 9, 2022

(54) PRECISION ACTIVATION OF HIV-SPECIFIC CTLS TO ELIMINATE REACTIVATED LATENT T CELLS

(71) Applicant: Albert Einstein College of Medicine, Bronx, NY (US)

(72) Inventors: Harris Goldstein, Teaneck, NJ (US); Steven C. Almo, Pelham, NY (US)

(73) Assignee: Albert Einstein College of Medicine, Bronx, NY (US)

( * ) Notice: Subject to any disclaimer, the term of this patent is extended or adjusted under 35 U.S.C. 154(b) by 0 days.

(21) Appl. No.: 16/603,306

(22) PCT Filed: Apr. 2, 2018

(86) PCT No.: PCT/US2018/025621
§ 371 (c)(1),
(2) Date: Oct. 7, 2019

(87) PCT Pub. No.: WO2018/187190
PCT Pub. Date: Oct. 11, 2018

(65) Prior Publication Data
US 2021/0107967 A1    Apr. 15, 2021

Related U.S. Application Data

(60) Provisional application No. 62/482,235, filed on Apr. 6, 2017.

(51) Int. Cl.
| | |
|---|---|
| *A61P 31/18* | (2006.01) |
| *C07K 14/045* | (2006.01) |
| *C07K 14/52* | (2006.01) |
| *C12N 15/62* | (2006.01) |
| *A61K 38/00* | (2006.01) |
| *C07K 14/74* | (2006.01) |
| *C07K 7/00* | (2006.01) |

(52) U.S. Cl.
CPC ........ *C07K 14/70539* (2013.01); *A61P 31/18* (2018.01); *C07K 7/00* (2013.01); *C07K 14/045* (2013.01); *C07K 14/52* (2013.01); *C12N 15/62* (2013.01); *A61K 38/00* (2013.01); *C07K 2319/33* (2013.01)

(58) Field of Classification Search
None
See application file for complete search history.

(56) References Cited

U.S. PATENT DOCUMENTS

| | | | |
|---|---|---|---|
| 2004/0209363 A1 | 10/2004 | Watts et al. | |
| 2017/0058015 A1* | 3/2017 | Seidel, III | ............... A61P 35/00 |
| 2017/0176435 A1* | 6/2017 | Seidell, III | ........... C12Q 1/6881 |

FOREIGN PATENT DOCUMENTS

| | | | |
|---|---|---|---|
| WO | 2014052545 A2 | 4/2014 | |
| WO | 2015112541 A2 | 7/2015 | |
| WO | WO 2015/112541 A2 * | 7/2015 | |
| WO | 2015195531 A2 | 12/2015 | |
| WO | 2016200782 A1 | 12/2016 | |

OTHER PUBLICATIONS

PCT International Search Report and Written Opinion dated Sep. 17, 2018 in connection with PCT International Application No. PCT/US2018/025621.

* cited by examiner

*Primary Examiner* — Nianxiang Zou
(74) *Attorney, Agent, or Firm* — Fox Rothschild LLP

(57) ABSTRACT

Compositions and methods to increase the in vivo capacity of CD8+ T cells to kill HIV-infected and reactivated latent HIV-infected T cells (LHITC) to functionally cure HIV infection or improve the clinical course. Compositions and methods to increase the in vivo capacity of CD8+ T cells to kill CMV or CMV-infected cells are also provided.

24 Claims, 8 Drawing Sheets
Specification includes a Sequence Listing.

PRECISION ACTIVATION OF HIV-SPECIFIC CTLS TO ELIMINATE REACTIVATED LATENT T CELLS

CROSS-REFERENCE TO RELATED APPLICATIONS

This application is a U.S. national phase of PCT International Patent Application No. PCT/US2018/025621, filed Apr. 2, 2018, which claims benefit of U.S. Provisional Application No. 62/482,235, filed Apr. 6, 2017, the contents of which are hereby incorporated by reference.

BACKGROUND OF THE INVENTION

Throughout this application various publications are referred to, including by number. Full citations for these references may be found at the end of the specification. The disclosures of these publications, and all patents, patent application publications and books referred to herein, are hereby incorporated by reference in their entirety into the subject application to more fully describe the art to which the subject invention pertains.

Novel biologic and cell-based therapies to boost anti-HIV immune responses to control and cure HIV infection are revolutionizing the treatment of HIV but are limited by continuing challenges including: 1) the serious side effects and fatalities that are a consequence of the untargeted global immune stimulation by immunomodulatory biologics; 2) the logistical challenges in the scalability and toxicities of cell-based therapies which require ex vivo transduction and expansion such as adoptive therapy with chimeric antigen receptor engineered T (CAR-T) cells genetically modified to express HIV-specific antibody fragments linked to T cell activation cytoplasmic signaling domains; 3) the lack of flexible platforms to rapidly and efficiently identify and explore new immunomodulatory approaches and mechanisms to focally amplify HIV-specific cytotoxic T lymphocytes (CTL) function.

A high priority goal for HIV research is to develop approaches that would lead to a cure or lifelong remission of HIV infection. It would be most desirable to achieve a sterilizing cure with no detectible viremia or active production of HIV as was achieved in one unique individual, the "Berlin patient" after a hematopoietic stem cell (HSC) transplant from a delta32 CCR5 mutation homozygous donor and repopulation with donor-derived CD4+ T cells resistant to R5-tropic HIV infection (1,2). However, this approach was unsuccessful in 6 other HIV-infected individuals either due to outgrowth and subsequent X4-tropic HIV viremia or death from transplant complications and/or their underlying disease (3,4). An alternate strategy is a functional cure where viral replication is controlled by the immune system so that there is no degradation of the CD4+ T cell population as observed in untreated HIV-1-infected elite controllers (EC) who maintain undetectable viral loads and normal CD4+ T cell levels (5,6). Several lines of evidence have indicated that the control is mediated by a qualitatively effective CD8+ T cell response (7,8) as manifested by the polyfunctionality (9), lytic granule content (10,12) and/or T-bet expression (13) by their HIV-specific CTL. An alternative approach, termed "shock and kill", provides a functional cure by eradicating or markedly depleting the latent reservoir (LR) of very long-lived quiescent HIV-infected CD4+ resting memory T cells capable of reintroducing systemic HIV-1 infection after cART interruption by reactivating the latent cells to make them visible to the immune system for elimination (14,15). However, clinical application of this approach has been limited by the minimal in vivo activity of current latency reversing agents (LRA) and the inability of the treated individuals' intrinsic anti-HIV-1 immune response to effectively eliminate the reactivated latent infected cells (16-20). The compromised killing capacity of HIV-specific CD8+ T cells in cART-treated HIV-infected individuals is reversible as indicated by the restoration of the in vitro capacity of CTL from HIV-infected individuals to eliminate reactivated latent infected cells by ex vivo antigen-specific stimulation (21) and by incubation with dendritic cells loaded with HIV-derived peptides (22). Thus, treatments to increase the in vivo capacity of CD8+ T cells to kill HIV-infected and reactivated latent HIV-infected T cells (LHITC) should greatly enhance the efficacy of successful protocols to functionally cure HIV infection or alter the clinical course to that observed in elite controllers.

The present invention addresses this need for new therapeutics to specifically eliminate HIV-infected and reactivated latent HIV-infected T cells.

SUMMARY OF THE INVENTION

A multimeric polypeptide is provided comprising:
a) a first polypeptide comprising, in order from N-terminus to C-terminus:
i) an HIV epitope;
ii) a first major histocompatibility complex (MHC) polypeptide; and
b) a second polypeptide comprising, in order from N-terminus to C-terminus:
i) a second MHC polypeptide; and
ii) optionally an immunoglobulin (Ig) Fc polypeptide or a non-Ig scaffold,
wherein the multimeric polypeptide comprises one or more costimulatory domains and/or a cytokine, wherein the one or more costimulatory domain or cytokine is:
A) at the C-terminus of the first polypeptide;
B) at the N-terminus of the second polypeptide;
C) at the C-terminus of the second polypeptide; or
D) at the C-terminus of the first polypeptide and at the N-terminus of the second polypeptide,
and wherein the costimulatory domain is a GITRL, 4-1BBL, anti-CD28, sFv anti-CD28, CD30, LIGHT, OX40L, CD40, 4-1BBL, GITRL, ICOSL, CD70, CD80, CD86, or interferon or wherein the costimulatory domain activates CD28, HVEM, OX40, CD40L, 4-1BB, GITR, ICOS or CD27,
or wherein the cytokine is IL-2, IL-7, IL-12, IL-15 or IL-21 or wherein the cytokine activates a receptor for IL-2, IL-7, IL-12, IL-15 or IL-21.

A nucleic acid is provided comprising a nucleotide sequence encoding a recombinant polypeptide,
i) wherein the recombinant polypeptide comprises, in order from N-terminus to C-terminus:
a) an HIV epitope;
b) a first major histocompatibility complex (MHC) polypeptide;
c) one or more costimulatory domain polypeptides and/or cytokine polypeptides;
d) a proteolytically cleavable linker or a ribosome skipping signal;

e) a second MHC polypeptide; and
f) an immunoglobulin (Ig) Fc polypeptide; or
ii) wherein the recombinant polypeptide comprises, in order from N-terminus to C-terminus:
a) an HIV epitope;
b) a first MHC polypeptide;
c) a proteolytically cleavable linker or a ribosome skipping signal;
d) one or more costimulatory domain polypeptides and/or cytokine polypeptides;
e) a second MHC polypeptide; and
f) an Ig Fc polypeptide,
wherein the costimulatory domain polypeptide is a GITRL, 4-1BBL, anti-CD28, sFv anti-CD28, CD30, LIGHT, OX40L, CD40, 4-1BBL, GITRL, ICOSL, CD70, CD80, CD86, or interferon or wherein the costimulatory domain polypeptide activates CD28, HVEM, OX40, CD40L, 4-1BB, GITR, ICOS or CD27 or wherein the cytokine is IL-2, IL-7, IL-12, IL-15 or IL-21 or wherein the cytokine activates a receptor for IL-2, IL-7, IL-12, IL-15 or IL-21.

A recombinant expression vector is provided comprising a nucleic acid as described herein.

A host cell genetically modified with the recombinant expression vector as described herein is provided.

Also provided is a composition comprising:
a) a first nucleic acid comprising a nucleotide sequence encoding a first polypeptide comprising, in order from N-terminus to C-terminus:
i) an HIV epitope;
ii) a first MHC polypeptide; and
iii) one or more costimulatory domain polypeptides; and
b) a first nucleic acid comprising a nucleotide sequence encoding a second polypeptide comprising, in order from N-terminus to C-terminus:
i) a second MHC polypeptide; and
ii) an Ig Fc polypeptide
wherein the costimulatory domain polypeptide is a GITR, 4-1BBL, anti-CD28, sFv anti-CD28, CD30, LIGHT, OX40L, CD40, ICOSL CD70, CD80, CD86, or interferon, or wherein the costimulatory domain polypeptide activates CD28, HVEM, OX40, CD40L, 4-1BB, GITRL, ICOS or CD27 or wherein the cytokine is IL-2, IL-7, IL-12, IL-15 or IL-21 or wherein the cytokine activates the receptors for IL-2, IL-7, IL-12, IL-15 or IL-21.

Also provided is a composition comprising:
a) a first nucleic acid comprising a nucleotide sequence encoding a first polypeptide comprising, in order from N-terminus to C-terminus:
i) an HIV epitope; and
ii) a first MHC polypeptide; and
b) a first nucleic acid comprising a nucleotide sequence encoding a second polypeptide comprising, in order from N-terminus to C-terminus:
i) one or more costimulatory domain polypeptides and/or cytokine polypeptides;
ii) a second MHC polypeptide; and
iii) an Ig Fc polypeptide
wherein the costimulatory domain polypeptide is a GITRL, 4-1BBL, sFv anti-CD28, anti-CD28, CD30, LIGHT, OX40L, CD40, ICOSL CD70, CD80, CD86, or interferon or wherein the costimulatory domain polypeptide activates CD28, HVEM, OX40, CD40L, 4-1BB, GITR, ICOS or CD27 or wherein the cytokine is IL-2, IL-7, IL-12, IL-15 or IL-21 or wherein the cytokine activates the receptors for IL-2, IL-7, IL-12, IL-15 or IL-21.

A host cell genetically modified with the composition as described herein is provided.

A method is provided of producing a multimeric polypeptide, the method comprising:
a) culturing the host cell as described herein in vitro in a culture medium under conditions such that the host cell synthesizes the multimeric polypeptide; and
b) isolating the multimeric polypeptide from the host cell and/or from the culture medium.

In an embodiment, the second polypeptide comprises an affinity tag, and wherein said isolating comprises contacting the multimeric polypeptide produced by the cell with a binding partner for the affinity tag, wherein the binding partner is immobilized, thereby immobilizing the multimeric polypeptide. In an embodiment, the method comprises eluting the immobilized multimeric polypeptide.

A method is provided of selectively modulating the activity of an HIV epitope-specific T cell, the method comprising contacting the T cell with a first multimeric polypeptide as described herein, wherein said contacting selectively modulates the activity of the HIV epitope-specific T cell. In an embodiment, the costimulatory domain is an anti-CD28 domain. In an embodiment, the HIV epitope is SLFN-TIAVL.

A method is provided of selectively modulating the activity of an HIV epitope-specific T cell, the method comprising contacting the T cell with a plurality of first multimeric polypeptides as described herein, wherein said contacting selectively modulates the activity of the HIV epitope-specific T cell.

A method is provided of selectively modulating the activity of an HIV epitope-specific T cell in an individual, the method comprising administering to the individual an effective amount of the multimeric polypeptide as described herein effective to selectively modulate the activity of an HIV epitope-specific T cell in an individual.

A method is provided method of treating an HIV infection in an individual, the method comprising administering to the individual an amount of
a) the multimeric polypeptide as described herein; or
b) one or more recombinant expression vectors comprising nucleotide sequences encoding the multimeric polypeptide as described herein; or
c) one or more mRNAs comprising nucleotide sequences encoding the multimeric polypeptide as described herein, effective to modulate activity of HIV epitope-specific T cell in an individual.

Also provided is a method of treating an HIV infection in an individual, the method comprising administering to the individual an amount of
a) a plurality of multimeric polypeptides as described herein, wherein at least two of the plurality of multimeric polypeptides comprise different HIV epitope sequences, or
b) one or more recombinant expression vectors comprising nucleotide sequences encoding a plurality of multimeric polypeptides as described herein, wherein at least two of the plurality of multimeric polypeptides comprise different HIV epitope sequences; or
c) one or more mRNAs comprising nucleotide sequences encoding a plurality of multimeric polypeptides as described herein, wherein at least two of the plurality of multimeric polypeptides comprise different HIV epitope sequences,
effective to modulate activity of HIV epitope-specific T cell in an individual.

A composition is provided comprising:
a) the multimeric polypeptide as described herein; and
b) a pharmaceutically acceptable excipient.

Also provided is a composition comprising:
a) the nucleic acid as described herein or the recombinant expression vector as described herein; and
b) a pharmaceutically acceptable excipient.

Also provided is a method of reactivating a latent HIV infected T-cell in an individual, the method comprising administering to the individual an amount of a multimeric polypeptide comprising
a) a first polypeptide comprising, in order from N-terminus to C-terminus:
i) an HIV epitope;
ii) a first major histocompatibility complex (MHC) polypeptide; and
b) a second polypeptide comprising, in order from N-terminus to C-terminus:
i) a second MHC polypeptide; and
ii) optionally an immunoglobulin (Ig) Fc polypeptide or a non-Ig scaffold,
wherein the multimeric polypeptide comprises one or more costimulatory domains and/or a cytokine, wherein the one or more costimulatory domain or cytokine is:
A) at the C-terminus of the first polypeptide;
B) at the N-terminus of the second polypeptide;
C) at the C-terminus of the second polypeptide; or
D) at the C-terminus of the first polypeptide and at the N-terminus of the second polypeptide,
and wherein the costimulatory domain is a GITRL, 4-1BBL, anti-CD28, sFv anti-CD28, CD30, LIGHT, OX40L, CD40, 4-1BBL, GITRL, ICOSL, CD70, CD80, CD86, or interferon or wherein the costimulatory domain activates CD28, HVEM, OX40, CD40L, 4-1BB, GITR, ICOS or CD27,
or wherein the cytokine is IL-2, IL-7, IL-12, IL-15 or IL-21 or wherein the cytokine activates a receptor for IL-2, IL-7, IL-12, IL-15 or IL-21,
wherein at least one of the first and second MHC polypeptides is HLA-mismatched with the individual, effective to reactivating a latent HIV infected T-cell in an individual.

DETAILED DESCRIPTION OF THE INVENTION

Figures 1A, 1B:
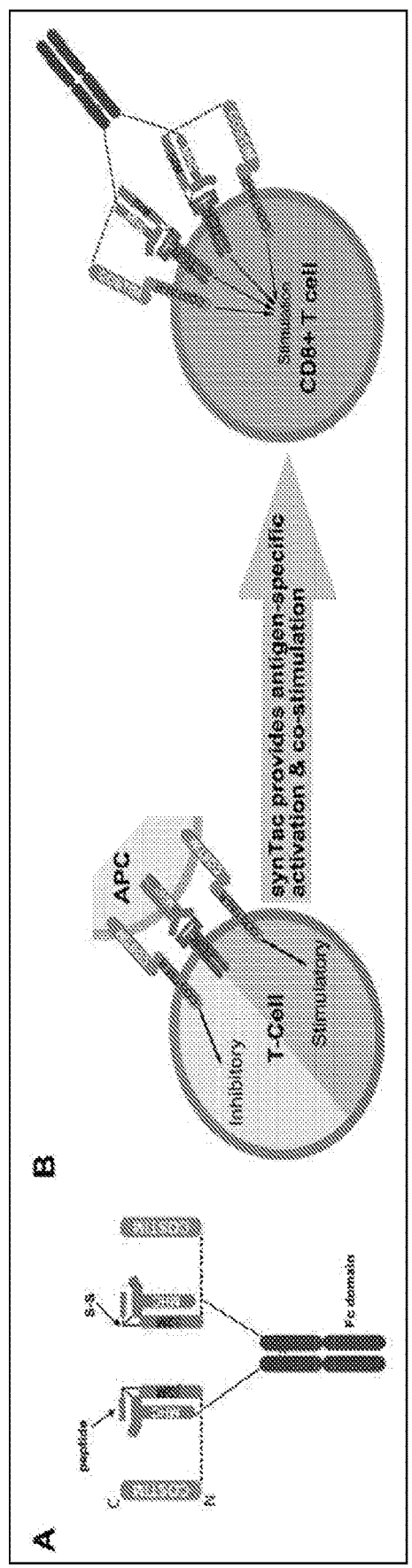
FIG. 1A-1B. synTac: an artificial immunological synapse for T cell activation. (A) synTac Fc-fusion molecule structure. The Fc domain is a native covalent homodimer, formed by interaction of two identical immunoglobulin CH2-CH3 domains (Fc) stabilized through two disulfide bonds between CH2 domains (two thin lines). To link the costimulatory domain (COSTIM) or cytokine to the sc-pMHC, the peptide was linked to the amino-terminus of the β2M and the MHC heavy chain (MHC) through disulfide bridges (S—S) and the amino terminus of the COSTIM or cytokine to the carboxy terminal extension of the β2M and linked the MHC to the Fc region. (B) synTac Fc-fusion molecule function. In the classic two signal T cell activation paradigm (left panel), an initial antigen-specific signal between TCR and its cognate MHC-peptide presented by an Antigen Presenting Cell (APC) is followed by secondary stimulation through costimulatory molecule engagement and/or cytokine receptor engagement. The synTac molecule (right panel) provides both signals to activate T cells using a defined Class I MHC and peptide linked to a costimulatory domain (COSTIM) or cytokine mimicking the natural response to elicit a focused clonal, not global, T cell response with highly specific T cell targeting of the cognate MHC-peptide peptide and costimulatory signals.

A multimeric polypeptide is provided comprising:
a) a first polypeptide comprising, in order from N-terminus to C-terminus:
i) an HIV epitope;
ii) a first major histocompatibility complex (MHC) polypeptide; and
b) a second polypeptide comprising, in order from N-terminus to C-terminus:
i) a second MHC polypeptide; and
ii) optionally an immunoglobulin (Ig) Fc polypeptide or a non-Ig scaffold,
wherein the multimeric polypeptide comprises one or more costimulatory domains, and/or cytokine(s), wherein the one or more costimulatory domain is and/or cytokine(s):
A) at the C-terminus of the first polypeptide;
B) at the N-terminus of the second polypeptide;

C) at the C-terminus of the second polypeptide; or
D) at the C-terminus of the first polypeptide and at the N-terminus of the second polypeptide,
and wherein the costimulatory domain is a GITRL, 4-1BBL, anti-CD28, sFv anti-CD28, CD30, LIGHT, OX40L, CD40, ICOSL, CD70, CD80, CD86, or interferon, or wherein the costimulatory domain activates CD28, HVEM, OX40, CD40L, 4-1BB, GITR, ICOS or CD27 or wherein the cytokine is IL-2, IL-7,11-12, IL-15 or IL-21 or wherein the cytokine activates the receptors for IL-2, IL-7, IL-12, IL-15 or IL-21.

In an embodiment, the HIV epitope is a GAG epitope or a mutated GAG epitope.

In an embodiment, the multimeric polypeptide comprises:
a) a first polypeptide comprising, in order from N-terminus to C-terminus:
i) an epitope;
ii) a first MHC polypeptide; and
iii) one or more costimulatory domains; and
b) a second polypeptide comprising, in order from N-terminus to C-terminus:
i) a second MHC polypeptide; and
ii) an Ig Fc polypeptide.

In an embodiment, the multimeric polypeptide comprises:
a) a first polypeptide comprising, in order from N-terminus to C-terminus:
i) an epitope; and
ii) a first MHC polypeptide; and
b) a second polypeptide comprising, in order from N-terminus to C-terminus:
i) one or more costimulatory domains and/or cytokine;
iii) a second MHC polypeptide; and
ii) an immunoglobulin (Ig) Fc polypeptide.

In an embodiment, the multimeric polypeptide comprises:
a) a first polypeptide comprising, in order from N-terminus to C-terminus:
i) an epitope; and
ii) a first MHC polypeptide; and
b) a second polypeptide comprising, in order from N-terminus to C-terminus:
i) a second MHC polypeptide; and
ii) an Ig Fc polypeptide; and
iii) one or more costimulatory domains.

In an embodiment, the multimeric polypeptide comprises:
a) a first polypeptide comprising, in order from N-terminus to C-terminus:
i) an epitope; and
ii) a first MHC polypeptide; and
b) a second polypeptide comprising, in order from N-terminus to C-terminus:
i) a second MHC polypeptide; and
ii) one or more costimulatory domains.

In an embodiment, the multimeric polypeptide comprises:
a) a first polypeptide comprising, in order from N-terminus to C-terminus:
i) an epitope; and
ii) a first MHC polypeptide; and
b) a second polypeptide comprising, in order from N-terminus to C-terminus:
i) one or more costimulatory domains; and
ii) a second MHC polypeptide.

In an embodiment, the multimeric polypeptide comprises:
a) a first polypeptide comprising, in order from N-terminus to C-terminus:
i) an epitope;
ii) a first MHC polypeptide; and
iii) one or more costimulatory domains; and
b) a second polypeptide comprising, in order from N-terminus to C-terminus:
i) a second MHC polypeptide.

In an embodiment, the non-Ig scaffold is an XTEN polypeptide, a transferrin polypeptide, an Fc receptor polypeptide, an elastin-like polypeptide, a silk-like polypeptide, or a silk-elastin-like polypeptide.

In an embodiment, the first MHC polypeptide is a $\beta$2-microglobulin polypeptide; and wherein the second MHC polypeptide is an MHC class I heavy chain polypeptide.

In an embodiment, the $\beta$2-microglobulin polypeptide comprises a human $\beta$2-microglobulin sequence.

In an embodiment, the MHC class I heavy chain polypeptide is an HLA-A, an HLA-B, an HLA-C, or an HLA-E heavy chain.

In an embodiment, the MHC class I heavy chain polypeptide comprises an HLA-E heavy chain.

In an embodiment, the first MHC polypeptide is an MHC Class II alpha chain polypeptide; and wherein the second MHC polypeptide is an MHC class II beta chain polypeptide.

In an embodiment, the HIV epitope comprises the amino acid sequence SLYNTVATL, SLFNTVATL, SLFNTIATL, SLFNTVAVL, SLYNTIATL, SLYNTVAVL, SLYNTIAVL, SLFNTVATL, SLFNAVATL, SLFNAVAVL or SLFNTIAVL (SEQ ID NOS. 1-11, respectively).

In an embodiment, the second MHC polypeptide is linked via a linker peptide at a C terminus thereof to an Ig Fc polypeptide, and wherein the Ig Fc polypeptide is an IgG1 Fc polypeptide, an IgG2 Fc polypeptide, an IgG3 Fc polypeptide, an IgG4 Fc polypeptide, an IgA Fc polypeptide, or an IgM Fc polypeptide.

In an embodiment, the Ig Fc polypeptide comprises a human Ig Fc sequence.

In an embodiment, the first polypeptide and the second polypeptide are non-covalently associated.

In an embodiment, the first polypeptide and the second polypeptide are covalently linked.

In an embodiment, the covalent linkage is via a disulfide bond.

In an embodiment, the first MHC polypeptide or a linker between the epitope and the first MHC polypeptide comprises an amino acid substitution to provide a first Cys residue, and the second MHC polypeptide comprises an amino acid substitution to provide a second Cys residue, and wherein the disulfide linkage is between the first and the second Cys residues.

In an embodiment, the multimeric polypeptide comprises a first linker interposed between the epitope and the first MHC polypeptide. In an embodiment, the linker or first linker comprises a GGGGS (SEQ ID NO.12) repeat sequence. In an embodiment, the linker or first linker comprises a sequence GCGAS (SEQ ID NO.13). In an embodiment, the linker or first linker comprises a sequence -GCGAS-(GGGS)$_4$- (SEQ ID NO. 14).

In an embodiment, the multimeric polypeptide comprises 2 or more a costimulatory domain polypeptides. In an embodiment, the 2 or more costimulatory domain polypeptides are in tandem.

In an embodiment, the multimeric polypeptide comprises 3 costimulatory domain polypeptides. In an embodiment, the 3 costimulatory domain polypeptides are each a 4-1BBL polypeptide.

In an embodiment, the first costimulatory domain polypeptide is linked via a first linker peptide to a second costimulatory domain polypeptide, and wherein the second costimulatory domain polypeptide is linked via a second linker peptide to the third costimulatory domain polypeptide, and wherein the third costimulatory domain polypeptide is linked via a third linker peptide to the first MHC polypeptide.

In an embodiment, the first costimulatory domain polypeptide is linked via a first linker peptide at its C terminus to the second costimulatory domain polypeptide, and wherein the second costimulatory domain polypeptide is linked via a second linker peptide at its C terminus to a third costimulatory domain polypeptide, and wherein the third costimulatory domain polypeptide is linked via a third linker peptide at its C terminus to the first MHC polypeptide.

In an embodiment, the first linker peptide and second linker peptide each comprise multiple repeats of the sequence GGGGS. In an embodiment, first linker peptide and second linker peptide each comprises more than 5 repeats of the sequence GGGGS. In an embodiment, first linker peptide and second linker peptide each comprises 7 repeats of the sequence GGGGS. In an embodiment, first linker peptide and second linker peptide each comprises 9 repeats of the sequence GGGGS In an embodiment, the MHC polypeptide is a β2M peptide.

In an embodiment, the multimeric polypeptide comprises a third polypeptide, wherein the third polypeptide comprises a costimulatory domain polypeptide comprising an amino acid sequence having at least 90% amino acid sequence identity to the costimulatory domain of the first polypeptide or the second polypeptide. In an embodiment, the third polypeptide is non-covalently linked to the first polypeptide.

In an embodiment, the second polypeptide comprises, in order from N-terminus to C-terminus:
i) the second MHC polypeptide;
ii) the Ig Fc polypeptide; and
iii) an affinity tag.

In an embodiment, the multimeric polypeptide comprises an anti-CD28. In an embodiment, the anti-CD28, as recited herein, comprises an anti-CD28 antibody or CD28 receptor-binding fragment thereof. In an embodiment, the anti-CD28 is an alpha-CD28 antibody. In an embodiment, the anti-CD28 antibody is agonistic. In an embodiment, the multimeric polypeptide comprises a sFv anti-CD28. In an embodiment, the sFv anti-CD28, as recited herein, comprises (i) a variable region which recognizes and binds a CD28 receptor, and (ii) at least a portion of the transmembrane region of a B7 receptor. For non-limiting examples of sFv anti-CD28, see U.S. Pat. No. 6,699,715, hereby incorporated by reference in its entirety.

A nucleic acid is provided comprising a nucleotide sequence encoding a recombinant polypeptide,
i) wherein the recombinant polypeptide comprises, in order from N-terminus to C-terminus:
a) an HIV epitope;
b) a first major histocompatibility complex (MHC) polypeptide;
c) one or more costimulatory domain polypeptides;
d) a proteolytically cleavable linker or a ribosome skipping signal;
e) a second MHC polypeptide; and
f) an immunoglobulin (Ig) Fc polypeptide; or
ii) wherein the recombinant polypeptide comprises, in order from N-terminus to C-terminus:
a) an HIV epitope;
b) a first MHC polypeptide;
c) a proteolytically cleavable linker or a ribosome skipping signal;
d) one or more costimulatory domain polypeptides;
e) a second MHC polypeptide; and
f) an Ig Fc polypeptide,
wherein the costimulatory domain polypeptide is a GITRL, 4-1BBL, anti-CD28, sFv anti-CD28, CD30, LIGHT, OX40L, CD40, ICOSL, CD70, CD80, CD86, or interferon, or wherein the costimulatory domain polypeptide activates CD28, HVEM, OX40, CD40L, 4-1BB, GITR, ICOS or CD27 or wherein the cytokine is IL-2, IL-7, IL-12, IL-15 or IL-21 or wherein the cytokine activates the receptors for IL-2, IL-7, IL-12, IL-15 or IL-21.

In an embodiment, the first MHC polypeptide is a β2-microglobulin polypeptide; and wherein the second MHC polypeptide is an MHC class I heavy chain polypeptide. In an embodiment, the β2-microglobulin polypeptide comprises a human β2-microglobulin polypeptide sequence.

In an embodiment, the MHC class I heavy chain polypeptide is an HLA-A, HLA-B, HLA-C, or HLA-E heavy chain. In an embodiment, the MHC class I heavy chain polypeptide comprises a human HLA-E heavy chain. In an embodiment, the first MHC polypeptide is an MHC Class II alpha chain polypeptide; and wherein the second MHC polypeptide is an MHC class II beta chain polypeptide.

In an embodiment, the HIV epitope comprises the amino acid sequence SLYNTVATL, SLFNTVATL, SLFNTIATL, SLFNTVAVL, SLYNTIATL, SLYNTVAVL, SLYNTIAVL, SLFNTVATL, SLFNAVATL, SLFNAVAVL or SLFNTIAVL (SEQ ID NOS: 1-11, respectively).

In an embodiment, the Ig Fc polypeptide is an IgG1 Fc polypeptide, an IgG2 Fc polypeptide, an IgG3 Fc polypeptide, an IgG4 Fc polypeptide, an IgA Fc polypeptide, or an IgM Fc polypeptide. In an embodiment, the Ig Fc polypeptide comprises a human Ig Fc sequence.

In an embodiment, the proteolytically cleavable linker or ribosome skipping signal comprises an amino acid sequence selected from:

```
                                            (SEQ ID NO: 15)
             a) LEVLFQGP;

(SEQ ID NO: 16)
             b) ENLYTQS;

c) a furin cleavage site;

(SEQ ID NO: 17)
             d) LVPR;

(SEQ ID NO: 18)
             e) GSGATNFSLLKQAGDVEENPGP;

(SEQ ID NO: 19)
             f) GSGEGRGSLLTCGDVEENPGP;

(SEQ ID NO: 20)
             g) GSGQCTNYALLKLAGDVESNPGP;
             and (SEQ ID NO: 21)
             h) GSGVKQTLNFDLLKLAGDVESNPGP.
```

In an embodiment, the recombinant polypeptide comprises, in order from N-terminus to C-terminus:
a) a first leader peptide;
b) the epitope;
c) the first MHC polypeptide;
d) one or more costimulatory domain polypeptides comprising GITRL, 4-1BBL, or anti-CD28;
e) the proteolytically cleavable linker or ribosome skipping signal;

f) a second leader peptide;
g) the second MHC polypeptide; and
h) the immunoglobulin (Ig) Fc polypeptide.

In an embodiment, the first leader peptide and the second leader peptide is a β2-M leader peptide.

In an embodiment, the nucleotide sequence is operably linked to a transcriptional control element.

In an embodiment, the transcriptional control element is a promoter that is functional in a eukaryotic cell.

In an embodiment, the first MHC polypeptide or a linker between the epitope and the first MHC polypeptide comprises an amino acid substitution to provide a first Cys residue, and the second MHC polypeptide comprises an amino acid substitution to provide a second Cys residue, and wherein the first and the second Cys residues provide for a disulfide linkage between the first MHC polypeptide and the second MHC polypeptide.

A recombinant expression vector is provided comprising a nucleic acid as described herein.

In an embodiment, the vector is a viral vector or a non-viral vector.

A host cell genetically modified with the recombinant expression vector as described herein is provided. In an embodiment, the host cell is in vitro. In an embodiment, the host cell is genetically modified such that the cell does not produce an endogenous MHC β2-microglobulin polypeptide. In an embodiment, the host cell is a T lymphocyte.

Also provided is a composition comprising:
a) a first nucleic acid comprising a nucleotide sequence encoding a first polypeptide comprising, in order from N-terminus to C-terminus:
 i) an HIV epitope;
 ii) a first MHC polypeptide; and
 iii) one or more costimulatory domain polypeptides; and
b) a first nucleic acid comprising a nucleotide sequence encoding a second polypeptide comprising, in order from N-terminus to C-terminus:
 i) a second MHC polypeptide; and
 ii) an Ig Fc polypeptide
wherein the costimulatory domain polypeptide is a GITRL, 4-1BBL, anti-CD28, sFv anti-CD28, CD30, LIGHT, OX40L, CD40, ICOSL, CD70, CD80, CD86, or interferon, or wherein the costimulatory domain polypeptide activates CD28, HVEM, OX40, CD40L, 4-1BB, GITR, ICOS or CD27 or wherein the cytokine is IL-2, IL-7, 11-12, IL-15 or IL-21 or wherein the cytokine activates the receptors for IL-2, IL-7, IL-12, IL-15 or IL-21.

Also provided is a composition comprising:
a) a first nucleic acid comprising a nucleotide sequence encoding a first polypeptide comprising, in order from N-terminus to C-terminus:
 i) an HIV epitope; and
 ii) a first MHC polypeptide; and
b) a first nucleic acid comprising a nucleotide sequence encoding a second polypeptide comprising, in order from N-terminus to C-terminus:
 i) one or more costimulatory domain polypeptides;
 ii) a second MHC polypeptide; and
 iii) an Ig Fc polypeptide
wherein the costimulatory domain polypeptide is a GITRL, 4-1BBL, sFv anti-CD28, anti-CD28, CD30, LIGHT, OX40L, CD40, ICOSL, CD70, CD80, CD86, or interferon, or wherein the costimulatory domain polypeptide activates CD28, HVEM, OX40, CD40L, 4-1BB, GITR, ICOS or CD27 or wherein the cytokine is IL-2, IL-7, 11-12, IL-15 or IL-21 or wherein the cytokine activates the receptors for IL-2, IL-7, IL-12, IL-15 or IL-21.

In an embodiment, the HIV epitope comprises the amino acid sequence SLYNTVATL, SLFNTVATL, SLFNTIATL, SLFNTVAVL, SLYNTIATL, SLYNTVAVL, SLYNTIAVL, SLFNTVATL, SLFNAVATL, SLFNAVAVL or SLFNTIAVL (SEQ ID NOS.1-11, respectively). In an embodiment, the first and/or the second nucleic acid is present in a recombinant expression vector.

A host cell genetically modified with the composition as described herein is provided.

A method is provided of producing a multimeric polypeptide, the method comprising:
a) culturing the host cell as described herein in vitro in a culture medium under conditions such that the host cell synthesizes the multimeric polypeptide; and
b) isolating the multimeric polypeptide from the host cell and/or from the culture medium.

In an embodiment, the second polypeptide comprises an affinity tag, and wherein said isolating comprises contacting the multimeric polypeptide produced by the cell with a binding partner for the affinity tag, wherein the binding partner is immobilized, thereby immobilizing the multimeric polypeptide. In an embodiment, the method comprises eluting the immobilized multimeric polypeptide.

A method is provided of selectively modulating the activity of an HIV epitope-specific T cell, the method comprising contacting the T cell with a first multimeric polypeptide as described herein, wherein said contacting selectively modulates the activity of the HIV epitope-specific T cell. In an embodiment, the costimulatory domain is an anti-CD28 domain. In an embodiment, the HIV epitope is SLFNTIAVL.

In an embodiment, the multimeric polypeptide activates a naïve HIV epitope specific CD8+ T cell. In an embodiment, the method further comprises contacting an activated HIV epitope specific CD8+ T cell with a second multimeric polypeptide as described herein wherein the costimulatory domain is a GITRL, 4-1BBL, CD30, LIGHT, OX40L, CD40, ICOSL, CD70, CD80, CD86, or interferon, or wherein the cytokine is IL-2, IL-7, IL-12, L-15 or IL-21 or wherein the cytokine activates the receptors for IL-2, IL-7, IL-12, IL-15 or IL-21.

In an embodiment, the contacting with the second multimeric polypeptide occurs at least 24 hours after the contacting with the first multimeric polypeptide. In an embodiment, the contacting with the second multimeric polypeptide occurs at least 5 days after the contacting with the first multimeric polypeptide. In an embodiment, the contacting with the second multimeric polypeptide occurs at least 6 days after the contacting with the first multimeric polypeptide. In an embodiment, the contacting with the second multimeric polypeptide occurs at least 7 days after the contacting with the first multimeric polypeptide. In an embodiment, the contacting with the second multimeric polypeptide occurs 7-14 days after the contacting with the first multimeric polypeptide.

In an embodiment, the T cell is a cytolytic T cell. In an embodiment, the T cell is a CD8+ T cell. In an embodiment, said contacting is in vitro. In an embodiment, said contacting is in vivo.

A method is provided of selectively modulating the activity of an HIV epitope-specific T cell, the method comprising contacting the T cell with a plurality of first multimeric polypeptides as described herein, wherein said contacting selectively modulates the activity of the HIV epitope-specific T cell.

In an embodiment, the costimulatory domain is an anti-CD28 domain.

In an embodiment, the plurality of first multimeric polypeptides comprises at least one having an HIV epitope SLFNTIAVL and at least one having an escape variant HIV epitope which differs from the sequence SLFNTIAVL at 1, 2 or 3 residues thereof.

In an embodiment, the multimeric polypeptides activate naïve HIV epitope specific CD8+ T cells.

In an embodiment, the method further comprises contacting an activated HIV epitope specific CD8+ T cell with a second plurality of multimeric polypeptides as described herein wherein the costimulatory domain activates a HVEM, OX40, CD40L, 4-1BB, GITR, ICOS or CD27 or wherein the cytokine activates the receptors for IL-2, IL-7, IL-12, IL-15 or IL-21.

In an embodiment, the contacting with the second plurality occurs at least 24 hours after the contacting with the first plurality. In an embodiment, the contacting with the second plurality occurs at least 5 days after the contacting with the first plurality. In an embodiment, the contacting with the second plurality occurs at least 6 days after the contacting with the first plurality. In an embodiment, the contacting with the second plurality occurs at least 7 days after the contacting with the first plurality. In an embodiment, the contacting with the second plurality occurs 7-14 days after the contacting with the first plurality.

In an embodiment, the T cell is a cytolytic T cell. In an embodiment, the T cell is a CD8+ T cell.

In an embodiment, said contacting is in vitro. In an embodiment, said contacting is in vivo.

In an embodiment, the epitopes of the plurality of the first multimeric polypeptides have the same sequences as the epitopes of the plurality of the second multimeric polypeptides.

In an embodiment, the epitope of the first multimeric polypeptide has the same sequence as the epitope of the second multimeric polypeptide.

A method is provided of selectively modulating the activity of an HIV epitope-specific T cell in an individual, the method comprising administering to the individual an effective amount of the multimeric polypeptide as described herein effective to selectively modulate the activity of an HIV epitope-specific T cell in an individual.

In an embodiment, the costimulatory domain is an anti-CD28 domain.

In an embodiment, the HIV epitope is SLFNTIAVL and wherein the multimeric polypeptide activates a naïve HIV epitope specific CD8+ T cell.

In an embodiment, the method further comprises contacting an activated HIV epitope specific CD8+ T cell with a second multimeric polypeptide as described herein wherein the costimulatory domain activates a HVEM, OX40, CD40L, 4-1BB, GITR, ICOS or CD27 or wherein the cytokine activates the receptors for IL-2, IL-7, IL-12, IL-15 or IL-21. In an embodiment, the contacting with the second multimeric polypeptide occurs at least 24 hours after the contacting with the first multimeric polypeptide. In an embodiment, the contacting with the second multimeric polypeptide occurs at least 5 days after the contacting with the first multimeric polypeptide. In an embodiment, the contacting with the second multimeric polypeptide occurs at least 6 days after the contacting with the first multimeric polypeptide. In an embodiment, the contacting with the second multimeric polypeptide occurs at least 7 days after the contacting with the first multimeric polypeptide. In an embodiment, the contacting with the second multimeric polypeptide occurs 7-14 days after the contacting with the first multimeric polypeptide.

A method is provided method of treating an HIV infection in an individual, the method comprising administering to the individual an amount of
a) the multimeric polypeptide as described herein; or
b) one or more recombinant expression vectors comprising nucleotide sequences encoding the multimeric polypeptide as described herein; or
c) one or more mRNAs comprising nucleotide sequences encoding the multimeric polypeptide as described herein, effective to modulate activity of HIV epitope-specific T cell in an individual.

Also provided is a method of treating an HIV infection in an individual, the method comprising administering to the individual an amount of
a) a plurality of multimeric polypeptides as described herein, wherein at least two of the plurality of multimeric polypeptides comprise different HIV epitope sequences, or
b) one or more recombinant expression vectors comprising nucleotide sequences encoding a plurality of multimeric polypeptides as described herein, wherein at least two of the plurality of multimeric polypeptides comprise different HIV epitope sequences; or
c) one or more mRNAs comprising nucleotide sequences encoding a plurality of multimeric polypeptides as described herein, wherein at least two of the plurality of multimeric polypeptides comprise different HIV epitope sequences,
effective to modulate activity of HIV epitope-specific T cell in an individual.

In an embodiment, the HIV epitope comprises the amino acid sequence SLYNTVATL, SLFNTVATL, SLFNTIATL, SLFNTVAVL, SLYNTIATL, SLYNTVAVL, SLYNTIAVL, SLFNTVATL, SLFNAVATL, SLFNAVAVL or SLFNTIAVL (SEQ ID NOS. 1-11, respectively).

In an embodiment, said administering is subcutaneous. In an embodiment, said administering is intravenous. In an embodiment, said administering is intramuscular. In an embodiment, the administering is systemic.

In an embodiment, the administering is distal to a treatment site. In an embodiment, the administering is local. In an embodiment, the administering is at or near a treatment site.

A composition is provided comprising:
a) the multimeric polypeptide as described herein; and
b) a pharmaceutically acceptable excipient.

Also provided is a composition comprising:
a) the nucleic acid as described herein or the recombinant expression vector as described herein; and
b) a pharmaceutically acceptable excipient.

A method of reactivating a latent HIV infected T-cell in an individual, the method comprising administering to the individual an amount of a multimeric polypeptide comprising
a) a first polypeptide comprising, in order from N-terminus to C-terminus:
i) an HIV epitope;
ii) a first major histocompatibility complex (MHC) polypeptide; and
b) a second polypeptide comprising, in order from N-terminus to C-terminus:
i) a second MHC polypeptide; and
ii) optionally an immunoglobulin (Ig) Fc polypeptide or a non-Ig scaffold,
wherein the multimeric polypeptide comprises one or more costimulatory domains and/or a cytokine, wherein the one or more costimulatory domain or cytokine is:

A) at the C-terminus of the first polypeptide;
B) at the N-terminus of the second polypeptide;
C) at the C-terminus of the second polypeptide; or
D) at the C-terminus of the first polypeptide and at the N-terminus of the second polypeptide,
and wherein the costimulatory domain is a GITRL, 4-1BBL, anti-CD28, sFv anti-CD28, CD30, LIGHT, OX40L, CD40, 4-1BBL, GITRL, ICOSL, CD70, CD80, CD86, or interferon or wherein the costimulatory domain activates CD28, HVEM, OX40, CD40L, 4-1BB, GITR, ICOS or CD27,
or wherein the cytokine is IL-2, IL-7, IL-12, IL-15 or IL-21 or wherein the cytokine activates a receptor for IL-2, IL-7, IL-12, IL-15 or IL-21,
wherein at least one of the first and second MHC polypeptides is HLA-mismatched with the individual, effective to reactivating a latent HIV infected T-cell in an individual.

In an embodiment, the at least one first and second MHC polypeptides HLA-mismatched with the individual, is allogeneic to the individual. In an embodiment, the MHC polypeptide which is HLA-mismatched is an MHC Class I polypeptide. In an embodiment, the MHC polypeptide which is HLA-mismatched is an HLA-E. In an embodiment, the MHC polypeptide which is HLA-mismatched is an MHC Class II polypeptide.

In an embodiment, the method further comprises subsequently administering an amount of a second multimeric polypeptide as described herein, wherein at least one of the first and second MHC polypeptides is HLA-mismatched with the individual, and wherein the at least one of the first and second MHC polypeptides is a different type of Class I or Class II MHC polypeptide from a first administered Class I or Class II MHC polypeptide HLA-mismatched with the individual.

In an embodiment, the method further comprises subsequently administering an amount of an anti-HIV therapy so as to treat reactivated latent HIV infected T-cell in the individual.

A multimeric polypeptide is provided comprising:
a) a first polypeptide comprising, in order from N-terminus to C-terminus:
i) a CMV epitope;
ii) a first major histocompatibility complex (MHC) polypeptide; and
b) a second polypeptide comprising, in order from N-terminus to C-terminus:
i) a second MHC polypeptide; and
ii) optionally an immunoglobulin (Ig) Fc polypeptide or a non-Ig scaffold,
wherein the multimeric polypeptide comprises one or more costimulatory domains, and/or cytokine(s),
wherein the one or more costimulatory domain is and/or cytokine(s) are:
A) at the C-terminus of the first polypeptide;
B) at the N-terminus of the second polypeptide;
C) at the C-terminus of the second polypeptide; or
D) at the C-terminus of the first polypeptide and at the N-terminus of the second polypeptide,
and wherein the costimulatory domain is a GITRL, 4-1BBL, anti-CD28, sFv anti-CD28, CD30, LIGHT, OX40L, CD40, ICOSL, CD70, CD80, CD86, or interferon, or wherein the costimulatory domain activates CD28, HVEM, OX40, CD40L, 4-1BB, GITR, ICOS or CD27 or wherein the cytokine is IL-2, IL-7, Il-12, IL-15 or IL-21 or wherein the cytokine activates the receptors for IL-2, IL-7, IL-12, IL-15 or IL-21.

In embodiments, the first MHC polypeptide is a β2-microglobulin polypeptide; and wherein the second MHC polypeptide is an MHC class I heavy chain polypeptide.

In embodiments, the β2-microglobulin polypeptide comprises a human β2-microglobulin sequence.

In embodiments, the MHC class I heavy chain polypeptide is an HLA-A, an HLA-B, an HLA-C, or an HLA-E heavy chain.

In embodiments, the MHC class I heavy chain polypeptide comprises an HLA-E heavy chain.

In embodiments, the first MHC polypeptide is an MHC Class II alpha chain polypeptide; and wherein the second MHC polypeptide is an MHC class II beta chain polypeptide.

A method is provided of treating a cytomegalovirus (CMV) infection in an individual, the method comprising administering to the individual an amount of
a) one or more multimeric polypeptides as described herein comprising a CMV epitope, or
b) one or more recombinant expression vectors comprising nucleotide sequences encoding a such multimeric polypeptides as described herein comprising a CMV epitope; or
c) one or more mRNAs comprising nucleotide sequences encoding multimeric polypeptides as described herein comprising a CMV epitope,
effective to modulate activity of CMV epitope-specific T cell in an individual.

Also provided is a nucleic acid comprising a nucleotide sequence encoding a recombinant polypeptide,
i) wherein the recombinant polypeptide comprises, in order from N-terminus to C-terminus:
a) a CMV epitope;
b) a first major histocompatibility complex (MHC) polypeptide;
c) one or more costimulatory domain polypeptides and/or cytokine(s);
d) a proteolytically cleavable linker or a ribosome skipping signal;
e) a second MHC polypeptide; and
f) an immunoglobulin (Ig) Fc polypeptide; or
ii) wherein the recombinant polypeptide comprises, in order from N-terminus to C-terminus:
a) a CMV epitope;
b) a first MHC polypeptide;
c) a proteolytically cleavable linker or a ribosome skipping signal;
d) one or more costimulatory domain polypeptides and/or cytokine(s);
e) a second MHC polypeptide; and
f) an Ig Fc polypeptide,
and wherein the costimulatory domain is a GITRL, 4-1BBL, anti-CD28, sFv anti-CD28, CD30, LIGHT, OX40L, CD40, 4-1BBL, GITRL, ICOSL, CD70, CD80, CD86, or interferon or wherein the costimulatory domain activates CD28, HVEM, OX40, CD40L, 4-1BB, GITR, ICOS or CD27,
or wherein the cytokine is IL-2, IL-7, IL-12, IL-15 or IL-21 or wherein the cytokine activates a receptor for IL-2, IL-7, IL-12, IL-15 or IL-21.

In an embodiment the nucleic acid is a recombinant expression vector or is an mRNA.

In an embodiment, the CMV is human CMV. In an embodiment, the CMV epitope comprises a pp65-protein epitope. Human CMV pp65-protein epitopes are known in the art, see e.g. Kondo et al., Blood. 2004 Jan. 15; 103(2): 630-8 (hereby incorporated by reference). In an embodiment, the CMV epitope comprises CMVpp65(495-503) NLVPMVATV. In an embodiment, the CMV epitope not an immunodominant CMV epitope.

In an embodiment, the individual being treated for CMV infection is also HIV-positive.

In an embodiment of the methods described herein reciting an individual, the individual is a human being.

In an embodiment of the methods described herein, the polypeptide can be administered as an active ingredient in a pharmaceutical composition. In an embodiment, the polypeptide is the only pharmaceutically active ingredient in the pharmaceutical composition. In an embodiment, the pharmaceutical composition comprises a pharmaceutical carrier.

In the methods described herein, administration of the polypeptide, or of a pharmaceutical composition comprising the polypeptide, can be auricular, buccal, conjunctival, cutaneous, subcutaneous, endocervical, endosinusial, endotracheal, enteral, epidural, via hemodialysis, interstitial, intrabdominal, intraamniotic, intra-arterial, intra-articular, intrabiliary, intrabronchial, intrabursal, intracardiac, intracartilaginous, intracaudal, intracavernous, intracavitary, intracerebral, intracisternal, intracorneal, intracoronary, intradermal, intradiscal, intraductal, intraepidermal, intraesophagus, intragastric, intravaginal, intragingival, intraileal, intraluminal, intralesional, intralymphatic, intramedullary, intrameningeal, intramuscular, intraocular, intraovarian, intraepicardial, intraperitoneal, intrapleural, intraprostatic, intrapulmonary, intrasinal, intraspinal, intrasynovial, intratendinous, intratesticular, intrathecal, intrathoracic, intratubular, intratumor, intratympanic, intrauterine, intravascular, intravenous, intraventricular, intravesical, intravitreal, laryngeal, nasal, nasogastric, ophthalmic, oral, oropharyngeal, parenteral, percutaneous, periarticular, peridural, rectal, inhalationally, retrobulbar, subarachnoid, subconjunctival, sublingual, submucosal, topically, transdermal, transmucosal, transplacental, transtracheal, ureteral, uretheral, and vaginal.

As used herein, "treating" an HIV infection means that one or more symptoms of the disease by which the disease is characterized, are reduced, ameliorated, prevented, or placed in a state of remission.

As used herein, "treating" a CMV infection means that one or more symptoms of the disease by which the disease is characterized, are reduced, ameliorated, prevented, or placed in a state of remission.

All combinations of the various elements described herein are within the scope of the invention unless otherwise indicated herein or otherwise clearly contradicted by context.

This invention will be better understood from the Experimental Details, which follow. However, one skilled in the art will readily appreciate that the specific methods and results discussed are merely illustrative of the invention as described more fully in the claims that follow thereafter.

EXPERIMENTAL DETAILS

Example 1

Herein are disclosed polypeptide molecules which focally boost the in vivo cytotoxic and inhibitory activity of HIV-specific CD8+ T cells to mediate the in vivo elimination of HIV-infected cells and reactivated latent HIV-infected T cells (LHITC). This approach can also stimulate a broadened CTL response which is required to eliminate LHITC infected with CTL immune escape variants because the synTac constructs can be loaded with defined mixtures of HIV peptides corresponding to unmutated epitopes and immune escape variants and linked to costimulatory (COSTIM) domains or cytokine capable of inducing costimulatory pathways to activate naïve and memory CD8 T cells such as the B7-CD28 and 4-1BB-4-1BBL pathways, or such as the IL-2, IL-7, IL-12, IL-15 or IL-21 pathways, respectively. This is crucial for effective clinical treatment because the vast majority of HIV in LHITC carry escape mutants which render them insensitive to killing by CTL directed at common immunodominant epitopes but susceptible to CTL activated by ex vivo stimulation with a mixture of Gag peptides or a conserved unmutated Gag epitope (e.g. WF9-WASRELERF) (23). This approach is extremely amenable to in vivo administration and provides a new therapeutic modality for the targeted boosting of potent HIV-specific CTL responses to provide immune control of infection. A resulting elite controller phenotype could effect the elimination of reactivated LHITC.

Multiple creative approaches to stimulate the immune system to kill tumor cells have revolutionized cancer treatment by utilizing strategies including the use of soluble comodulatory molecule ligands or antibodies to block coinhibitory T cell signaling pathways (24,25), bi-specific antibodies (BsAbs) to recruit effector cells (26,27) and free peptide antigens to stimulate immune responses (28). The most clinically advanced immunotherapeutic approaches modulate the immune checkpoint regulation of T cell immunity based on the two signal paradigm for the activation of T cells: 1) an antigen-specific signal transduced by the unique T cell receptor (TCR) clonotype generated by a genomic editing process during the differentiation of each T cell (29) after the TCR engages with its cognate peptide presented by MHC molecules and 2) a costimulatory signal generated by the engagement of costimulatory receptors expressed by T cells with their costimulatory ligands expressed by antigen presenting cells (APC). A crucial aspect of this paradigm is that in contrast to the unique TCR expressed by each T cell, the specific costimulatory molecules expressed by CD4+ and CD8+ T cells are identical and can be activated or suppressed to polyclonally activate tumor-specific T cell responses to treat cancers (30). Constructs consisting of the extracellular domains of these membrane-expressed comodulatory molecules act as agonists, exert potent inhibitory activity and have been FDA-approved for the treatment of autoimmune diseases. To focus the immunomodulatory effects of these biologics on the crucial effector T cell population to treat cancer and autoimmune diseases and to minimize toxicities associated with global modulation of the immune system, a class of biologics termed synTac (artificial immunological Synapse for T-cell Activation) have been developed, schematically represented in FIG. 1 which uses the specificity of cognate MHC:peptides to target specific TCRs to selectively activate antigen-specific T cell populations. This novel strategy focused on the treatment of cancer and autoimmune diseases integrates the specificity and potency of antigen-receptor and costimulatory signaling through a unique design, which covalently links single chain peptide-MHC (sc-pMHC) constructs to a defined costimulatory or coinhibitory molecule. The sc-pMHC domain (FIG. 1, labeled MHC) targets synTac to specific T cell clones, while the comodulatory domain (MOD) delivers stimulatory or inhibitory signals, resulting in targeted antigen-specific T cell engagement and activation of defined comodulatory molecules. The specific linkage strategy and spacers used for the synTac are the product of extensive evaluation of multiple alternative approaches. (See WO/2015/195531 A3, hereby incorporated by reference).

The single-chain synTac strategy presented herein provides a platform for the selective in vivo expansion of HIV-specific CD8+ T cells, effectively bypassing the considerable ex vivo constraints of adoptive T cell therapy and the lack of specificity associated with current biologics such as PD-1 inhibitors. Loading the sc-MHC in the SynTac constructs with different Gag-derived peptides, for example, enables the TCR-specific activation of a wide range of HIV-specific CTLs likely required to eliminate reactivated latent cells infected with HIV carrying immune escape epitopes (23). Generation of the most optimal CTL response may require T cell activation by specific costimulatory molecules such as GITR (31,32) which in mice induce protective in vivo CD8+ T cell responses to tumors (33) and accelerated clearance of chronic LCMV infection (34). The modular construction of the synTac enables linking of the sc-MHC domain to different comodulatory molecule binding proteins enabling evaluation of the functional impact of coactivation of HIV-specific CTL by diverse costimulatory molecules and thereby develop synTac constructs with the most potent CTL functional activity. This approach to augment in vivo HIV immunity is validated by significant data disclosed herein demonstrating the capacity to generate significant quantities of unique functional synTac protein therapeutic constructs which stimulate in vitro clonal human T cell activation and proliferation and in vivo T cell proliferation in humanized murine models.

The synTac platform was converted into an immunostimulatory molecule by covalently linking it to costimulatory ligands or cytokines using a "single chain fusion" design to covalently link the peptide to the MHC molecule through an engineered disulfide bond between the peptide linker position 2 (glycine to cysteine mutations, G2C) and tyrosine 84 (Y84C) on the heavy chain and the β2m chain to ensure specific presentation of the linked peptide and prevent undesired cross presentation of self-peptide (FIG. 2). The covalently linked costimulatory domain can be any known or approved antibody, antibody fragment or costimulatory molecule ligand reported to bind and activate any defined costimulatory molecules expressed by T cells. The covalently linked cytokine can be any known or approved cytokine antibody, antibody fragment or molecule ligand reported to bind and activate any defined cytokine receptors expressed by T cells. The Fc domain is used as the synTac construct scaffold because the Fc domains efficiently form homodimers that are stabilized through two disulfide bonds (illustrated as thin lines in FIG. 2), thereby enabling the synTac to cross-link TCR molecules and costimulatory molecules which more effectively triggers the TCR signal transduction cascade. In addition, the Fc domain folds independently and improves the stability, solubility and biological half-life of the fused partner and also enables the synTac molecules to be rapidly and efficiently purified by protein-G/A affinity chromatography (35).

Figures 2A, 2B, 2C:
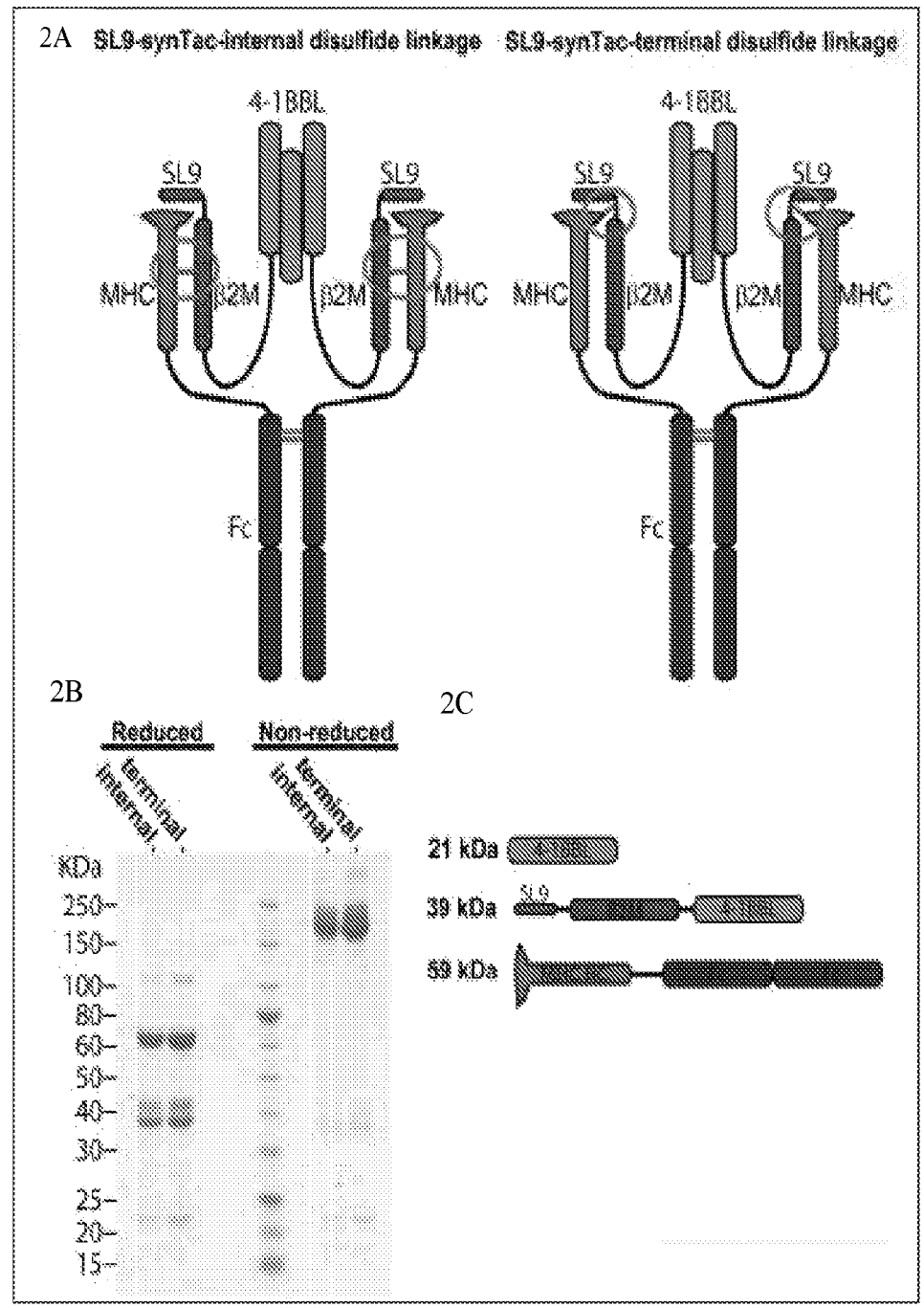
FIG. 2A-2C. Structure of SL9:4-1BBL synTac molecules. (2A) Schematics of two SL9:4-1BBL synTac molecules with engineered internal (synTac 251) or terminal (synTac 244) interchain disulfide bonds (circled in red) between the MHC and the SL9-β2m. (2B) Purified synTac molecules analyzed by SDS-PAGE under reducing and non-reducing conditions. (2C) Predicted synTac fragments and their molecular weight under reducing conditions.
Figures 3A, 3B, 3C:
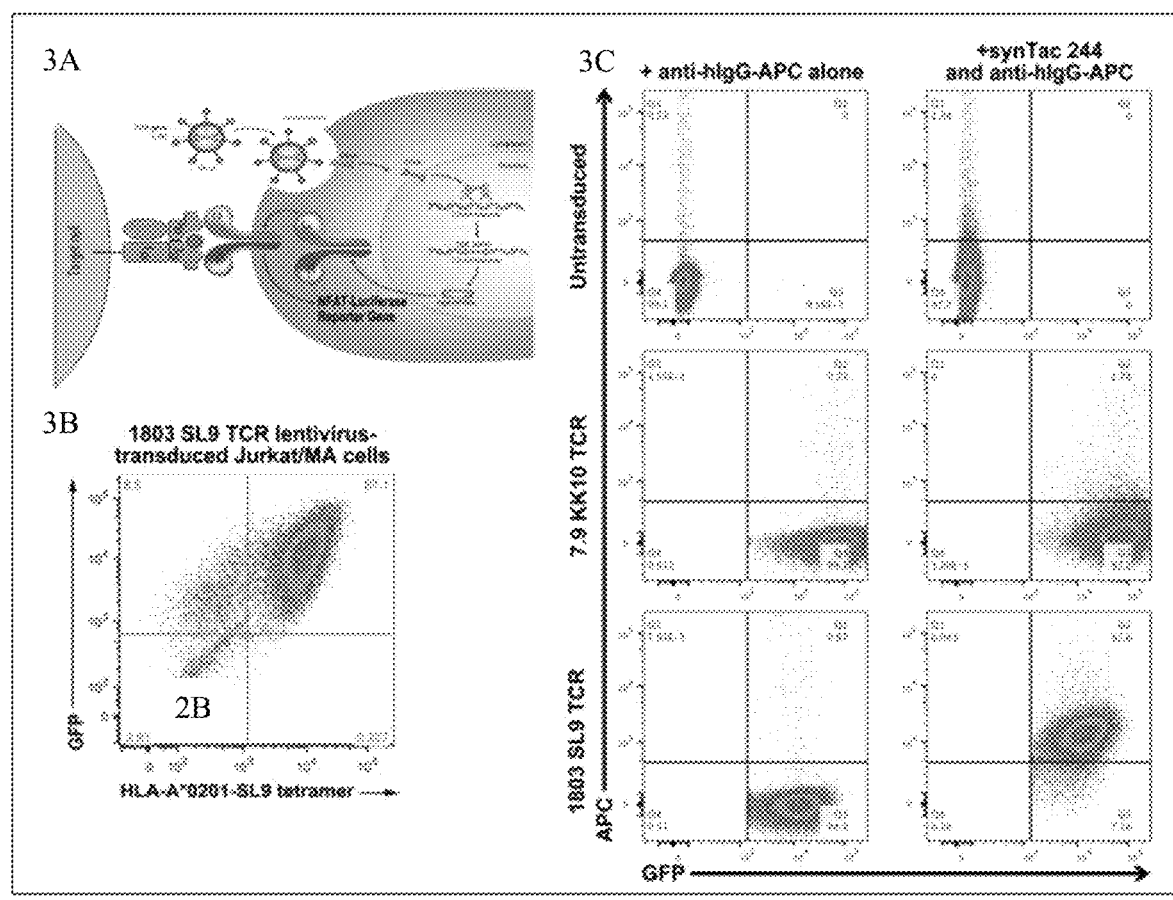
FIG. 3A-3C. SL9:4-1BBL synTac construct binds to Jurkat-MA cells expressing an SL9-specific TCR. (3A) Jurkat-MA CD8+ T cells transduced with the 1803 TCR lentivector express a GFP reporter and a SL9-specific TCR whose activation can be measured by quantifying luciferase activity. (3B) Binding of HLA-A2-SL9 tetramer to 1803 TCR lentivector-transduced Jurkat-MA cells. (3C) Binding of SL9:4-1BBL synTac molecule with engineered terminal interchain disulfide bonds (synTac 244) to untransduced cells (upper panels) or Jurkat-MA cells transduced with control 7.9KK10 TCR lentivector (middle panels) or 1803 SL9 TCR lentivector (lower panels).
Figures 4A, 4B:
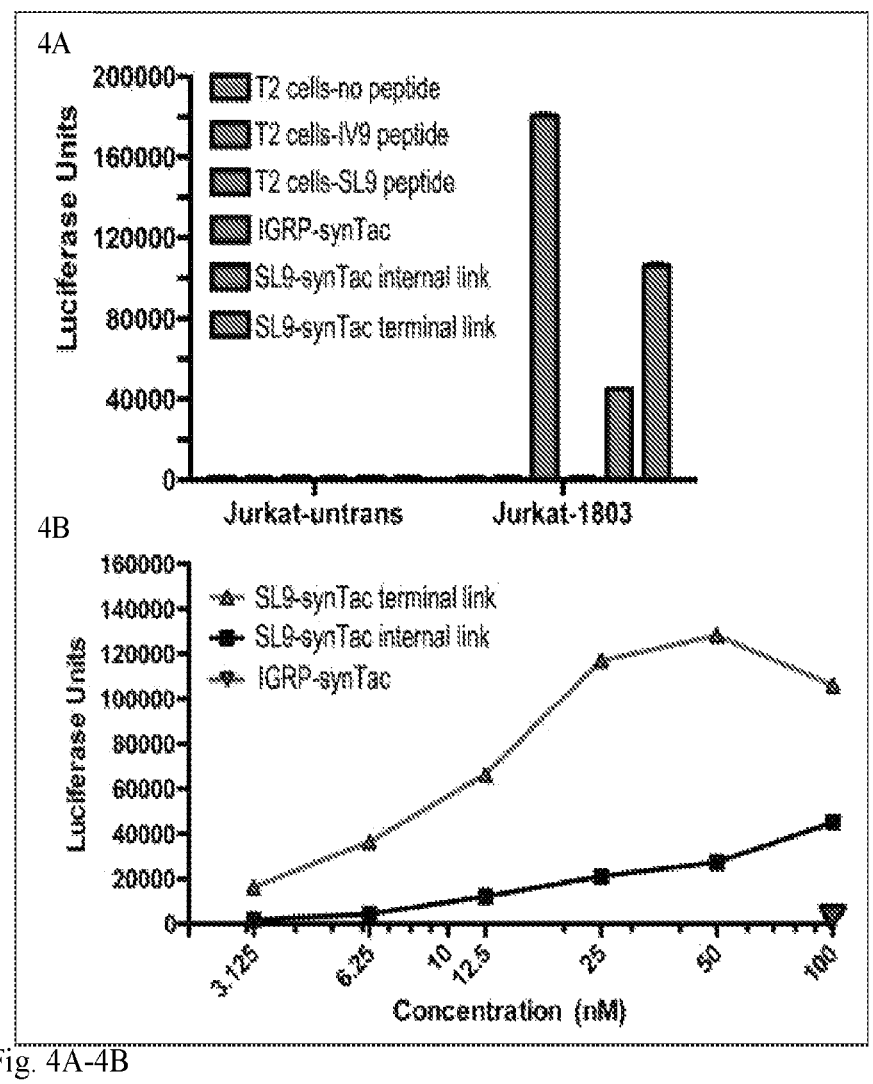
FIG. 4A-4B. SL9:4-1BBL synTac constructs activate Jurkat-MA cells expressing an SL9-specific TCR. (4A) Untransduced or 1803 TCR lentivector-transduced Jurkat/MA cells were incubated either with T2 cells loaded with no peptide, SL9 peptide or a control IV9 peptide or with the indicated synTac (100 nM). 16 hours later luciferase activity was measured. (4B) synTac at the indicated concentration was added to 1803 TCR-transduced Jurkat/MA cells and 16 hours later luciferase activity was measured.

Construction and characterization of HLA-A2-SL9:4-1BBL synTac fusion proteins (SL9:4-1BBL-synTac) and demonstration of their in vitro capacity to bind and activate SL9-specific TCRs: As a first step to evaluate the capacity of the synTac approach to boost the capacity of SL9-specific CTLs to eliminate reactivated LHITC, the optimal approach to link the MHC domain to the β2M was examined, either engineering a disulfide bond internally within the MHC and β2M proteins (FIG. 2A, left panel) or at the terminal ends of the MHC and β2M proteins (FIG. 2A, right panel). For the COSTIM domain 4-1BBL was used, which like other TNF superfamily members, forms a trimer and binds to three 4-1BB molecules (36). To form this trimer, a 4-1BBL chain was expressed with a flexible linker on each Fc chain and co-transfected the cells with a vector expressing 4-1BBL which trimerizes with the two 4-1BBL chains expressed by the synTac construct during protein assembly and folding (FIG. 2A). The appropriate assembly of the two synTac constructs was confirmed by analytic size-exclusion chromatography and by SDS-PAGE analysis of internal and terminal linked synTac under reducing and non-reducing conditions. The non-reduced samples displayed highly purified synTac at the predicted MW of ~200 kDa and reduced samples, after disruption of the disulfide bonds, displayed bands (FIG. 2B) running at the predicted MW (FIG. 2C). The SL9:4-1BBL-synTac activated CD8+ TCR-Jurkat/MA T cells containing an NFAT-regulated luciferase reporter gene after transduction with a lentivirus expressing an SL9-specific TCR, 1803 (FIG. 3A), as described (37), further demonstrating its structural integrity. After transduction, ~90% of Jurkat/MA T cells expressed the SL9-specific TCR by HLA-A*0201-SL9 tetramer staining (FIG. 3B). While untransduced Jurkat/MA cells and Jurkat/MA cells transduced with lentivirus expressing an irrelevant TCR (7.9 KK10) did not bind to the SL9:4-1BBL-synTac, over 90% of the Jurkat/MA transduced with the SL9-specific 1803 TCR lentivirus bound to the SL9:4-1BBL-synTac (FIG. 3C). Luciferase activity was potently induced only after incubation of the SL9 TCR-expressing Jurkat/MA cells with T2 cells loaded the SL9 peptide, but not the negative controls (FIG. 4A). Both SL9:4-1BBL-synTac constructs stimulated luciferase activity after incubation with the SL9 TCR-expressing Jurkat/MA cells indicating appropriate folding and loading of the sc-pMHC component (FIG. 4A), however the SL9:4-1BBL-synTac with the terminal linker more potently stimulated the SL9 TCR-expressing Jurkat/MA cells than SL9:4-1BBL-synTac with the internal linker (FIGS. 4A and 4B), perhaps because direct SL9 peptide linkage to the MHC enhances its presentation in the MHC cleft.

Figure 5:
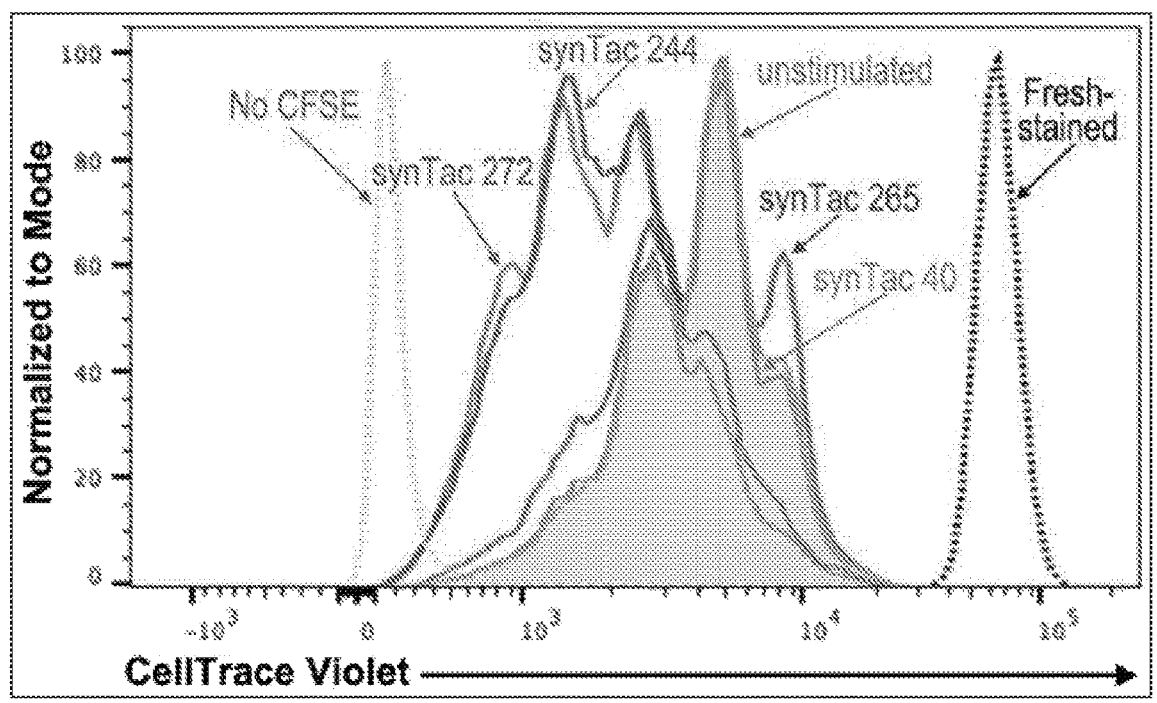
FIG. 5. SL9:4-1BBL synTac constructs stimulate proliferation of a SL9-specific CD8 CTL clone. CC2C cells stained with CellTrace Violet. were incubated with the indicated synTac (IGRP:4-1BBL (synTac 40), SL9:FLAG (synTac 265), SL9:4-1BBL (synTac 244) and SL9:covalent 4-1BBL (synTac 272) and IL-2 (50 U/ml) for 6 days. The cells were analyzed by flow cytometry along with freshly stained cells.
Figure 6:
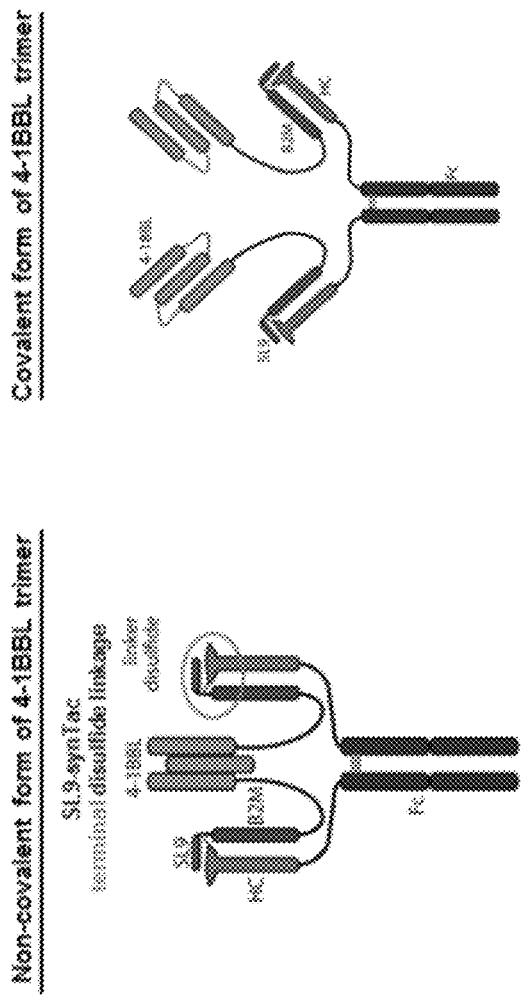
FIG. 6. Structure of SL9:4-1BBL synTac molecules with two forms of 4-1BBL trimer. The number of G4Sn repeats are 270:5, 271:7, and 272:9.
Figure 7:
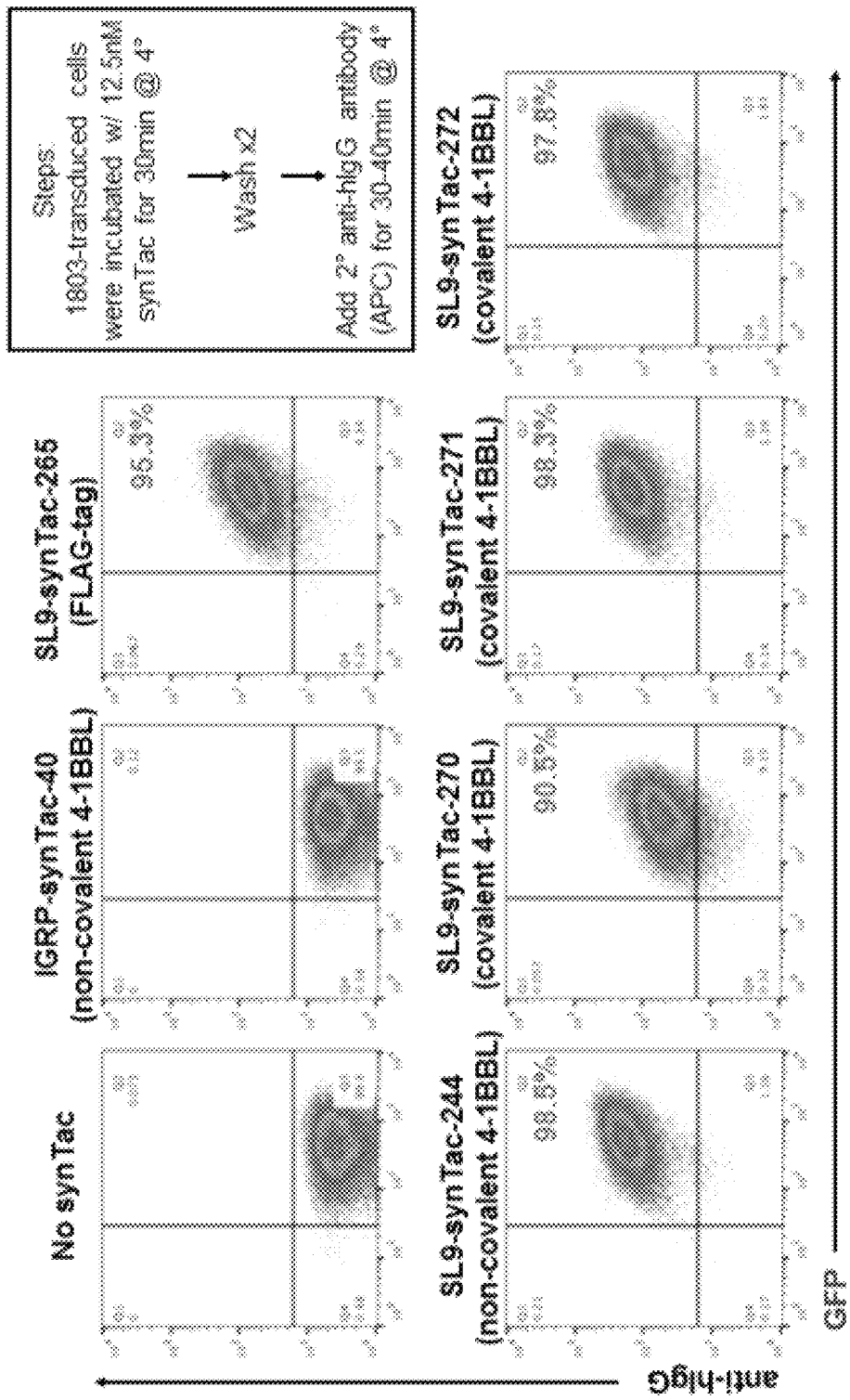
FIG. 7. SL9:4-1BBL synTac construct binds to Jurkat/MA cells expressing an sl9-specific TCR.

The SL9:4-1BBL-synTac binds and stimulates cytokine production and proliferation of an SL9-specific CTL clone. A SL9-specific CTL clone, CC2C38, was used to investigate the functional activity of the SL9:4-1BBL-synTac constructs and evaluate the beneficial impact of using flexible linkers to incorporate three 4-1BBL chains into the single chain construct to enable the self-contained assembly of two 4-1BBL trimers. CC2C cells, which express 4-1BB, were incubated with a control IGRP:4-1BBL synTac (synTac40), an SL9-specific synTac lacking the 4-1BBL domain (synTac 265), the SL9-specific synTac expressing a single 4-1BBL trimer (synTac-244) described above (FIGS. 3 and 4) and two newly synthesized SL9-specific synTac constructs expressing the three 4-1BBL chains covalently linked with different spacer lengths and forming two 4-1BBL trimers (synTac-271 and 272). The SL9-synTac lacking the 4-1BBL domain and the three SL9:4-1BBL-synTac constructs but not the IGRP:4-1BBL-synTac bound to the CC2C cells (data not chown). This indicated that while the SL9:pMHC domain contributed sufficient affinity to bind to the SSL9-specific TCR, the affinity of the 4-1BBL domain for its ligand was insufficient to mediate binding. Flow cytometry was used to examine the capacity of the synTac constructs to activate the CC2C cells and stimulate cytokine expression after overnight incubation with the indicated synTac. In contrast to the three SL9:4-1BBL-synTac constructs, neither the IGRP:4-1BBL-synTac nor the SL9-synTac lacking the 4-1BBL domain stimulated production of IFN-γ or TNF-α (data not shown). This demonstrated that engagement of the TCR alone by the SL9-synTac lacking the 4-1BBL domain or of the 4-1BB alone by the IGRP-synTac were insufficient for CTL activation. In contrast, the three SL9:4-1BBL-synTac constructs capable of engaging both the TCR and the 4-1BB proteins induced cytokine production. SL9:4-1BBL synTac constructs also stimulated proliferation of the CC2C cells. Flow cytometric analysis 6 days after freshly thawed CC2C cells were stained with CellTrace Violet (0.25 μM) and cultured with the indicated SynTac (100 nM) demonstrated that while IGRP:4-1BBL synTac (synTac 40) and SL9-specific synTac lacking the 4-1BBL domain (synTac 265) did not increase proliferation as compared to unstimulated CC2C cells, the SL9:4-1BBL-synTac with a non-covalently linked 4-1BBL chain (synTac-244) with a covalently linked chain (synTac-272) markedly stimulated CC2C cellular proliferation (FIG. 5).

Example 2

Use of Allogeneic synTac to Reactivate Latent HIV-Infected T Cells:

It has been proposed that cure of HIV infection would involve a "kick and kill" strategy which would reactivate latent HIV infected T cells (LHITC) followed by their elimination of the immune system (Archin NM1, Margolis D M. Emerging strategies to deplete the HIV reservoir. Curr Opin Infect Dis. 2014; 27:29-35. doi: 10.1097/QCO.0000000000000026). In addition to utilizing the synTac platform to stimulate potent T cell immunity to eliminate HIV infected cells and provide the "kill" component of a cure strategy, the synTac platform can also provide the "kick" component to reactivate LHITC. Thus, synTac molecules can be designed to provide the "kick" and the "kill" signals to cure HIV infection.

The results described below demonstrate that latent HIV-infected T cells are reactivated by exposure to allogeneic cells. However, it would be impractical and potentially dangerous to reactivate the latent reservoirs of HIV infected patients by injecting them with irradiated donor cells. Instead, the method disclosed herein reactivate HIV reservoirs in HIV-infected individuals, a crucial component of curing HIV infection, by injecting them with synTac expressing a mismatched MHC:peptide linked to either a costimulatory molecule and/or a cytokine. The allogenic MHC expressed by the synTac binds to T cell receptors and activates latent HIV infected cells. This activation is enhanced by the signal provided by the linked costimulatory molecule. If desired, the activation signal can be ameliorated in its induction of undesirable toxicity of over-activating the immune system and causing cytokine storm, by linking the allogeneic MHC:peptide to a co-inhibitory molecule such as PD-1L or TIM3 or an inhibitory cytokine such as TGF-β or IL-10. The MHC:peptide can be a Class I MHC molecule such as those encoded by the HLA-A, B, C or E genes or a Class II MHC molecule such as those encoded by HLA-DR, DQ or DP. The peptide can either be a foreign peptide or self-peptide which when presented by an allogeneic MHC molecule activates T cells. Since it is unlikely that one allogeneic molecule would activate all LHITC, patients could be treated serially with a plurality of synTac expressing different MHC molecules which in summation would reactivate all of the LHTIC and enable them to be eliminated and to cure HIV infection (as reported for the Berlin patient). Because the in vivo half-life of the synTac molecules is about 4 hours, this approach should provide transient allogeneic stimulation which should be safer than performing an MHC-mismatched bone marrow transplant, as performed for the Berlin patient, or injecting patients with irradiated allogeneic cells which may persist for weeks after injection.

Latent HIV-infected T cells (LHITC) are potently reactivated by exposure to allogeneic cells: T cells are central to the process of rejecting allografts based on their ability to recognize donor-derived antigens, called alloantigens. The alloantigens which activate the T cells against the allograft, i.e., are both major and minor histocompatibility antigens. The most potent alloantigens are class I (HLA-A, -B, -C) and class II (HLA-DR, -DP, -DQ) MHC molecules. While the function of MHC molecules is to present foreign antigens to T cells, alloantigen recognition can occur via the direct pathway of allorecognition where T cells "directly" recognize intact non-self MHC molecules present on the surface of donor cells (Matzinger P, Bevan M J (1977) Hypothesis: why do so many lymphocytes respond to major histocompatibility antigens? Cell Immunol 29:1-5, Daniel C, Horvath S, Allen P M (1998) A basis for alloreactivity: MHC helical residues broaden peptide recognition by the TCR. Immunity 8:543-552, Schneck J, Munitz T, Coligan J E, Maloy W L, Margulies D H, Singer A (1989) Inhibition of allorecognition by an H-2Kb-derived peptide is evidence for a T-cell binding region on a major histocompatibility complex molecule. Proc Natl Acad Sci USA 86:8516-8520, Berkowitz N, Braunstein N S (1992) T cell responses specific for subregions of allogeneic MHC molecules. J Immunol 148:309-317). In addition to activating specific T cells, by secreting stimulatory cytokines, alloactivation may also activate adjacent T cells. This is readily observed by the vigorous activation of T cells when they are mixed in culture with MHC-mismatched cells (Bach F H, Hirschhorn K (1964) Lymphocyte interaction: A potential histocompatibility test in vitro. Science 143:813-814).

Figure 8:
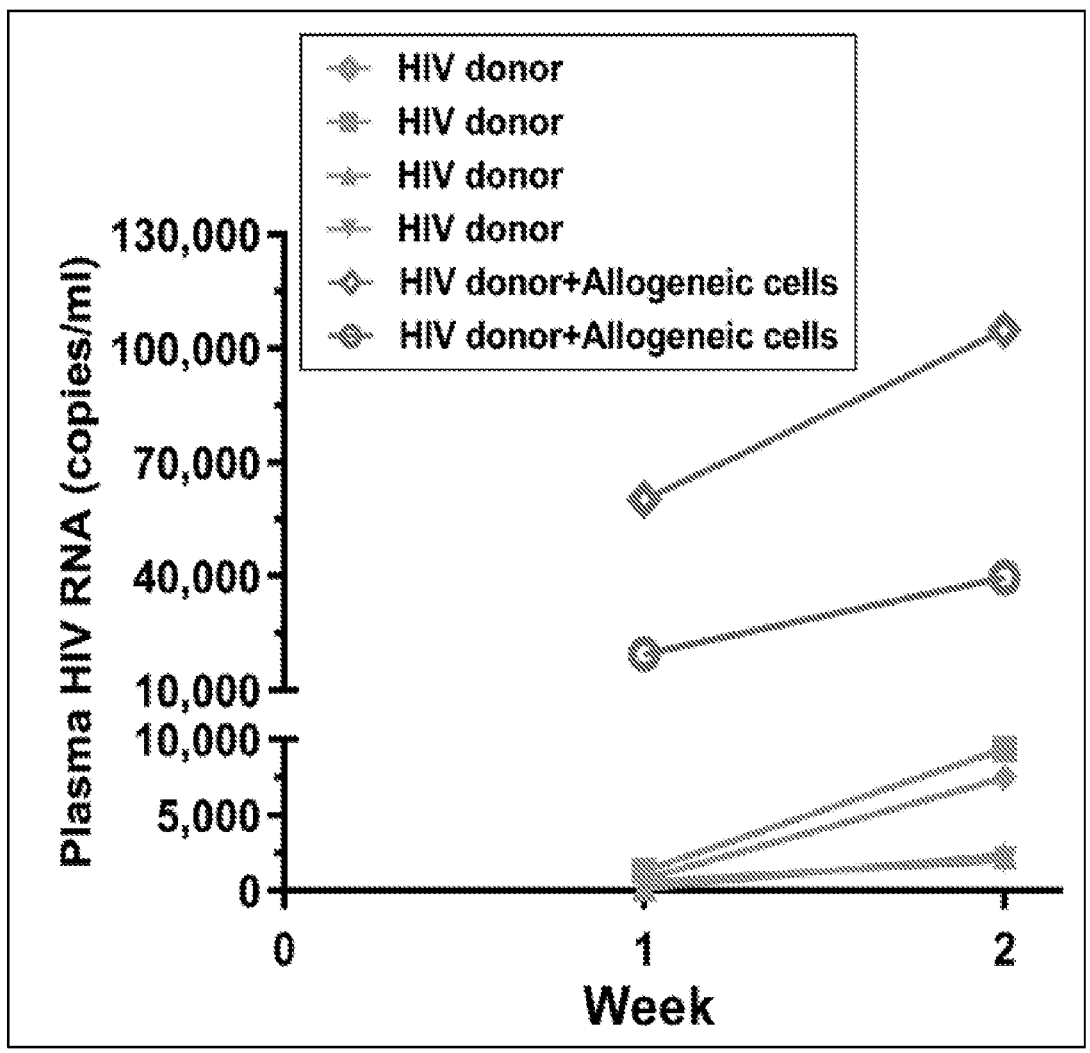
FIG. 8: In vivo reactivation of LHITC from an HIV-infected donor on suppressive ART. NSG mice were intrasplenically injected with PBMC from HIV-1-infected donor on suppressive cART (20×10$^6$ cells) alone (n=4 mice) or in combination with irradiated PBMC (5×10$^6$ cells) from an HLA-mismatched HIV naïve donor (n=2 mice). Plasma viremia was measured 1 week and 2 weeks after injection.

The inventors hypothesized that a major mechanism contributing to the cure of the "Berlin patient" (Hütter G I, Nowak D, Mossner M, Ganepola S, Müssig A, Allers K, Schneider T, Hofmann J, Kücherer C, Blau O, Blau I W, Hofmann W K, Thiel E. Long-term control of HIV by CCR5 Delta32/Delta32 stem-cell transplantation. N Engl J Med. 2009; 360:692-8. doi: 10.1056/NEJMoa0802905) was the "kick" provided by potent reactivation of latent HIV-infected T cells by allogeneic stimulation by donor cells which enabled them to be eliminated by the donor-derived immune system. To investigate whether exposure to allogeneic cells would provide a potent signal to reactivate LHITC, a novel in vivo humanized mouse model, termed the HIV-PAT-LAT mouse model, was used to examine reactivation and elimination of LHITC derived directly from HIV-infected donors. PBMCs isolated from a HIV-1-infected donor treated with suppressive cART ($20 \times 10^6$ cells) was intrasplenically injected alone or in combination with irradiated PBMC from an HLA-mismatched HIV naïve donor ($5 \times 10^6$ cells) into NSG mice. The mice were bled 1 week and 2 weeks after injection and plasma HIV RNA levels were determined by RT-qPCR (FIG. 8). In the NSG mice injected only with the HIV donor PBMC, HIV viremia was barely detectible in any of the mice one week after injection (mean=712 copies/ml) by two weeks after injection HIV viremia increased by over 7-fold (mean=5,315 copies/ml), likely reflecting spontaneous activation of latent HIV-infected cells as observed in HIV-infected individuals after ART interruption. In contrast, in mice injected with HIV donor PBMC and irradiated PBMC from an HLA-mismatched HIV naïve donor the presence of allogeneic cells markedly accelerated the recurrence and quantity of plasma viremia in the mice as compared mice only injected with the HIV donor PBMCs. The mean level of plasma viremia at 1 week and 2 weeks after injection were 39,757 and 72,136 copies/ml, respectively, as compared 712 and 5,315 copies/ml, respectively in NSG mice injected only with the HIV donor PBMCs. These results demonstrate that allogeneic cells potently reactivate latent HIV-infected cells.

Example 3

HIV epitope-specific synTac expand CTLs in the peripheral blood of HIV-infected individuals. HIV SL9-specific synTacs were constructed linked either to (i) FLAG (no signaling domain) or (ii) an agonistic antibody to CD28 ($\alpha$CD28) which stimulates the B7-CD28 pathway for activation of naïve T cells, or (iii) the 4-1BBL costimulatory ligand which activates the 4-1BB costimulatory pathway to potently expand and enhance tumor-specific CD8+ T cells (and is consequently used in many adoptive T cell-based cancer treatments). In addition, a CMV pp65-specific synTac linked to 4-1BBL was constructed. The capacity of the different SL9 synTac structural variants and the pp65 synTac to expand SL9-specific and pp65-specific CD8+ T cells, respectively, was demonstrated.

Purified CD8+ T cells from an HLA-A2*0201 HIV-infected human subject were incubated with the indicated synTac for 11 days. SL9 SynTac constructs linked to 4-1BBL or anti-CD28 costimulatory molecules specifically increased the SL9 tetramer+ population by ~3.5-fold and 2-fold, respectively, as compared to untreated CD8+ T cells. As a control, the SL9 synTac lacking a signaling domain (SL9-FLAG) or the pp65-4-BBL synTac did not significantly increase the SL9 tetramer+ population. pp65-4-1BBL synTac specifically expanded the pp65 tetramer+ population by >7.5-fold as compared to untreated CD8+ T cells without significantly increasing the SL9 tetramer+ population. Re-stimulating the CD8+ T cells with the SL9-4-1BBL synTac after 16 days of culture doubled the fraction of SL9-specific CD8+ T cells as compared to CD8+ T cells only stimulated at the initiation of culture, and increased it by almost 20-fold as compared to unstimulated CD8+ T cells. This likely reflects expansion of memory CD8+ T cells.

The qualitative function of HIV-specific CTLs correlates with their ability to secrete multiple cytokines, such as IFN-$\gamma$ and TNF-$\alpha$, after activation. In this regard, the capacity of the SL9 synTacs to stimulate SL9-specific T cells was investigated by incubating an SL9-specific CD8+ T cell clone with the indicated synTacs overnight and then evaluating the CD8+ T cells for activation and cytotoxicity by measuring production of IFN-$\gamma$ and TNF-$\alpha$ and expression of CD107a molecules (an indicator of degranulation). Marked increases in IFN-$\gamma$, TNF-$\alpha$ and CD107a were observed after incubation with the SL9-4-1BBL and SL9-$\alpha$CD28 synTacs as compared to no significant increase after incubation with pp65-4-1BBL synTac and moderate increases after TCR-only activation by incubation with the SL9-FLAG synTac. Taken together these data indicate that the synTacs bind specifically to their cognate TCR and deliver the antigen-specific and costimulatory signals to stimulate proliferation of primary HIV-specific and CMV-specific CD8+ T cells from HIV-infected humans.

REFERENCES

1. Allers K, Hutter G, Hofmann J, Loddenkemper C, Rieger K, Thiel E, Schneider T. Evidence for the cure of HIV infection by CCR5Delta32/Delta32 stem cell transplantation. *Blood.* 2011; 117(10):2791-9. PubMed PMID: 21148083.
2. Hutter G, Nowak D, Mossner M, Ganepola S, Mussig A, Allers K, Schneider T, Hofmann J, Kucherer C, Blau O, Blau I W, Hofmann W K, Thiel E. Long-term control of HIV by CCR5 Delta32/Delta32 stem-cell transplantation. *The New England journal of medicine.* 2009; 360(7):692-8. PubMed PMID: 19213682.
3. Hutter G. More on shift of HIV tropism in stem-cell transplantation with CCR5 delta32/delta32 mutation. *The New England journal of medicine.* 2014; 371(25):2437-8. PubMed PMID: 25517721.
4. Kordelas L, Verheyen J, Beelen D W, Horn P A, Heinold A, Kaiser R, Trenschel R, Schadendorf D, Dittmer U, Esser S. Shift of HIV tropism in stem-cell transplantation with CCR5 Delta32 mutation. *The New England journal of medicine.* 2014; 371(9):880-2. PubMed PMID: 25162903.
5. O'Connell K A, Brennan T P, Bailey J R, Ray S C, Siliciano R F, Blankson J N. Control of HIV-1 in elite suppressors despite ongoing replication and evolution in plasma virus. *Journal of virology.* 2010; 84(14):7018-28. PubMed PMID: 20444904; PubMed Central PMCID: PMC2898225.
6. Pereyra F, Palmer S, Miura T, Block B L, Wiegand A, Rothchild A C, Baker B, Rosenberg R, Cutrell E, Seaman M S, Coffin J M, Walker B D. Persistent low-level viremia in HIV-1 elite controllers and relationship to immunologic parameters. *The Journal of infectious diseases.* 2009; 200(6):984-90. PubMed PMID: 19656066; PubMed Central PMCID: PMC3725728.
7. Saez-Cirion A, Lacabaratz C, Lambotte O, Versmisse P, Urrutia A, Boufassa F, Barre-Sinoussi F, Delfraissy J F, Sinet M, Pancino G, Venet A. HIV controllers exhibit potent CD8 T cell capacity to suppress HIV infection ex vivo and peculiar cytotoxic T lymphocyte activation phenotype. *Proceedings of the National Academy of Sciences of the United States of America.* 2007; 104(16):6776-81. PubMed PMID: 17428922; PubMed Central PMCID: PMC1851664.
8. Buckheit R W, 3rd, Siliciano R F, Blankson J N. Primary CD8+ T cells from elite suppressors effectively eliminate non-productively HIV-1 infected resting and activated CD4+ T cells. *Retrovirology.* 2013; 10:68. PubMed PMID: 23816179; PubMed Central PMCID: PMC3702406.
9. Betts M R, Nason M C, West S M, De Rosa S C, Migueles S A, Abraham J, Lederman M M, Benito J M, Goepfert P A, Connors M, Roederer M, Koup R A. HIV nonprogressors preferentially maintain highly functional HIV-specific CD8+ T cells. *Blood.* 2006; 107(12):4781-9. PubMed PMID: 16467198; PubMed Central PMCID: PMC1895811.
10. Migueles S A, Laborico A C, Shupert W L, Sabbaghian M S, Rabin R, Hallahan C W, Van Baarle D, Kostense S, Miedema F, McLaughlin M, Ehler L, Metcalf J, Liu S, Connors M. HIV-specific CD8+ T cell proliferation is coupled to perforin expression and is maintained in non-progressors. *Nature immunology.* 2002; 3(11):1061-8. PubMed PMID: 12368910.
11. Migueles S A, Osborne C M, Royce C, Compton A A, Joshi R P, Weeks K A, Rood J E, Berkley A M, Sacha J B, Cogliano-Shutta N A, Lloyd M, Roby G, Kwan R, McLaughlin M, Stallings S, Rehm C, O'Shea M A, Mican J, Packard B Z, Komoriya A, Palmer S, Wiegand A P, Maldarelli F, Coffin J M, Mellors J W, Hallahan C W, Follman D A, Connors M. Lytic granule loading of CD8+ T cells is required for HIV-infected cell elimination associated with immune control. *Immunity.* 2008; 29(6): 1009-21. PubMed PMID: 19062316; PubMed Central PMCID: PMC2622434.

12. Yang O O, Lin H, Dagarag M, Ng H L, Effros R B, Uittenbogaart C H. Decreased perforin and granzyme B expression in senescent HIV-1-specific cytotoxic T lymphocytes. *Virology.* 2005; 332(1):16-9. PubMed PMID: 15661136.

13. Hersperger A R, Martin J N, Shin L Y, Sheth P M, Kovacs C M, Cosma G L, Makedonas G, Pereyra F, Walker B D, Kaul R, Deeks S G, Betts M R. Increased HIV-specific CD8+ T-cell cytotoxic potential in HIV elite controllers is associated with T-bet expression. *Blood.* 2011; 117(14):3799-808. PubMed PMID: 21289310; PubMed Central PMCID: PMC3083297.

14. Siliciano J D, Kajdas J, Finzi D, Quinn T C, Chadwick K, Margolick J B, Kovacs C, Gange S J, Siliciano R F. Long-term follow-up studies confirm the stability of the latent reservoir for HIV-1 in resting CD4+ T cells. *Nature medicine.* 2003; 9(6):727-8. PubMed PMID: 12754504.

15. Archin N M, Keedy K S, Espeseth A, Dang H, Hazuda D J, Margolis D M. Expression of latent human immunodeficiency type 1 is induced by novel and selective histone deacetylase inhibitors. *Aids.* 2009; 23(14):1799-806. PubMed PMID: 19590405; PubMed Central PMCID: PMC3809117.

16. Archin N M, Eron J J, Palmer S, Hartmann-Duff A, Martinson J A, Wiegand A, Bandarenko N, Schmitz J L, Bosch R J, Landay A L, Coffin J M, Margolis D M. Valproic acid without intensified antiviral therapy has limited impact on persistent HIV infection of resting CD4+ T cells. *Aids.* 2008; 22(10):1131-5. PubMed PMID: 18525258; PubMed Central PMCID: PMC3863687.

17. Elliott J H, Wightman F, Solomon A, Ghneim K, Ahlers J, Cameron M J, Smith M Z, Spelman T, McMahon J, Velayudham P, Brown G, Roney J, Watson J, Prince M H, Hoy J F, Chomont N, Fromentin R, Procopio F A, Zeidan J, Palmer S, Odevall L, Johnstone R W, Martin B P, Sinclair E, Deeks S G, Hazuda D J, Cameron P U, Sekaly R P, Lewin S R. Activation of HIV transcription with short-course vorinostat in HIV-infected patients on suppressive antiretroviral therapy. *PLoS pathogens.* 2014; 10(10):e1004473. PubMed PMID: 25393648; PubMed Central PMCID: PMC4231123.

18. Routy J P, Tremblay C L, Angel J B, Trottier B, Rouleau D, Baril J G, Harris M, Trottier S, Singer J, Chomont N, Sekaly R P, Boulassel M R. Valproic acid in association with highly active antiretroviral therapy for reducing systemic HIV-1 reservoirs: results from a multicentre randomized clinical study. *HIV medicine.* 2012; 13(5): 291-6. PubMed PMID: 22276680.

19. Sagot-Lerolle N, Lamine A, Chaix M L, Boufassa F, Aboulker J P, Costagliola D, Goujard C, Pallier C, Delfraissy J F, Lambotte O, study A E. Prolonged valproic acid treatment does not reduce the size of latent HIV reservoir. *Aids.* 2008; 22(10):1125-9. PubMed PMID: 18525257.

20. Siliciano J D, Lai J, Callender M, Pitt E, Zhang H, Margolick J B, Gallant J E, Cofrancesco J, Jr., Moore R D, Gange S J, Siliciano R F. Stability of the latent reservoir for HIV-1 in patients receiving valproic acid. *The Journal of infectious diseases.* 2007; 195(6):833-6. PubMed PMID: 17299713.

21. Shan L, Deng K, Shroff N S, Durand C M, Rabi S A, Yang H C, Zhang H, Margolick J B, Blankson J N, Siliciano R F. Stimulation of HIV-1-specific cytolytic T lymphocytes facilitates elimination of latent viral reservoir after virus reactivation. *Immunity.* 2012; 36(3):491-501. PubMed PMID: 22406268; PubMed Central PMCID: PMC3501645.

22. Sung J A, Lam S, Garrido C, Archin N, Rooney C M, Bollard C M, Margolis D M. Expanded cytotoxic T-cell lymphocytes target the latent HIV reservoir. *The Journal of infectious diseases.* 2015; 212(2):258-63. PubMed PMID: 25589335; PubMed Central PMCID: PMC4490234.

23. Deng K, Pertea M, Rongvaux A, Wang L, Durand C M, Ghiaur G, Lai J, McHugh H L, Hao H, Zhang H, Margolick J B, Gurer C, Murphy A J, Valenzuela D M, Yancopoulos G D, Deeks S G, Strowig T, Kumar P, Siliciano J D, Salzberg S L, Flavell R A, Shan L, Siliciano R F. Broad CTL response is required to clear latent HIV-1 due to dominance of escape mutations. *Nature.* 2015; 517(7534):381-5. PubMed PMID: 25561180; PubMed Central PMCID: PMCPMC4406054.

24. Beck A, Reichert J M. Therapeutic Fc-fusion proteins and peptides as successful alternatives to antibodies. *mAbs.* 2011; 3(5):415-6. PubMed PMID: 21785279; PubMed Central PMCID: PMCPMC3225844.

25. Weiner L M, Surana R, Wang S. Monoclonal antibodies: versatile platforms for cancer immunotherapy. *Nature reviews Immunology.* 2010; 10(5):317-27. PubMed PMID: 20414205; PubMed Central PMCID: PMCPMC3508064.

26. Chames P, Baty D. Bispecific antibodies for cancer therapy: the light at the end of the tunnel? *mAbs.* 2009; 1(6):539-47. PubMed PMID: 20073127; PubMed Central PMCID: PMCPMC2791310.

27. Oates J, Hassan N J, Jakobsen B K. ImmTACs for targeted cancer therapy: Why, what, how, and which. *Mol Immunol.* 2015; 67(2 Pt A):67-74. PubMed PMID: 25708206.

28. Sharma C, Khan M A, Mohan T, Shrinet J, Latha N, Singh N. A synthetic chimeric peptide harboring human papillomavirus 16 cytotoxic T lymphocyte epitopes shows therapeutic potential in a murine model of cervical cancer. *Immunol Res.* 2014; 58(1):132-8. PubMed PMID: 24174302.

29. Robins H S, Srivastava S K, Campregher P V, Turtle C J, Andriesen J, Riddell S R, Carlson C S, Warren E H. Overlap and effective size of the human CD8+ T cell receptor repertoire. *Sci Transl Med.* 2010; 2(47):47ra64. PubMed PMID: 20811043; PubMed Central PMCID: PMC3212437.

30. Sharma P, Allison J P. The future of immune checkpoint therapy. *Science.* 2015; 348(6230):56-61. PubMed PMID: 25838373.

31. Kim J, Choi W S, Kang H, Kim H J, Suh J H, Sakaguchi S, Kwon B. Conversion of alloantigen-specific CD8+ T cell anergy to CD8+ T cell priming through in vivo ligation of glucocorticoid-induced TNF receptor. *Journal of immunology.* 2006; 176(9):5223-31. PubMed PMID: 16621987.

32. Ronchetti S, Nocentini G, Bianchini R, Krausz L T, Migliorati G, Riccardi C. Glucocorticoid-induced TNFR-related protein lowers the threshold of CD28 costimulation in CD8+ T cells. *Journal of immunology.* 2007; 179(9):5916-26. PubMed PMID: 17947665.

33. Cote A L, Zhang P, O'Sullivan J A, Jacobs V L, Clemis C R, Sakaguchi S, Guevara-Patino J A, Turk M J. Stimulation of the glucocorticoid-induced TNF receptor family-related receptor on CD8 T cells induces protective and 34. Pascutti M F, Geerman S, Slot E, van Gisbergen K P, Boon L, Arens R, van Lier R A, Wolkers M C, Nolte M A. Enhanced CD8 T cell responses through GITR-mediated costimulation resolve chronic viral infection. *PLoS pathogens.* 2015; 11(3):e1004675. PubMed PMID: 25738498; PubMed Central PMCID: PMCPMC4349659.
35. Lo K M, Sudo Y, Chen J, Li Y, Lan Y, Kong S M, Chen L, An Q, Gillies S D. High level expression and secretion of Fc-X fusion proteins in mammalian cells. *Protein Eng.* 1998; 11(6):495-500. PubMed PMID: 9725629.
36. Won E Y, Cha K, Byun J S, Kim D U, Shin S, Ahn B, Kim Y H, Rice A J, Walz T, Kwon B S, Cho H S. The structure of the trimer of human 4-1BB ligand is unique among members of the tumor necrosis factor superfamily. *The Journal of biological chemistry.* 2010; 285(12):9202-10. PubMed PMID: 20032458; PubMed Central PMCID: PMC2838339.
37. Joseph A, Zheng J H, Follenzi A, Dilorenzo T, Sango K, Hyman J, Chen K, Piechocka-Trocha A, Brander C, Hooijberg E, Vignali D A, Walker B D, Goldstein H. Lentiviral vectors encoding human immunodeficiency virus type 1 (HIV-1)-specific T-cell receptor genes efficiently convert peripheral blood CD8 T lymphocytes into cytotoxic T lymphocytes with potent in vitro and in vivo HIV-1-specific inhibitory activity. *Journal of virology.* 2008; 82(6):3078-89. PubMed PMID: 18184707; PubMed Central PMCID: PMC2258988.
38. Kan-Mitchell J, Bisikirska B, Wong-Staal F, Schaubert K L, Bajcz M, Bereta M. The HIV-1 HLA-A2-SLYNTVATL is a help-independent CTL epitope. *J Immunol.* 2004; 172(9):5249-61. PubMed PMID: 15100263.

---

What is claimed is:

1. A multimeric polypeptide comprising:
   a) a first polypeptide comprising, in order from N-terminus to C-terminus:
      i) a human immune deficiency virus (HIV) epitope;
      ii) a first major histocompatibility complex (MHC) polypeptide; and
   b) a second polypeptide comprising, in order from N-terminus to C-terminus:
      i) a second MHC polypeptide; and
      ii) optionally an immunoglobulin (Ig) Fc polypeptide or a non-Ig scaffold,
   wherein the N-terminus of the first MHC polypeptide and the N-terminus of the second MHC polypeptide are covalently linked; and
   wherein the multimeric polypeptide comprises one or more costimulatory domains and/or cytokine(s), wherein the one or more costimulatory domain and/or cytokine is:
   A) at the C-terminus of the first polypeptide;
   B) at the N-terminus of the second polypeptide;
   C) at the C-terminus of the second polypeptide; or
   D) at the C-terminus of the first polypeptide and at the N-terminus of the second polypeptide,
   and wherein the costimulatory domain is a GITRL, 4-1BBL, anti-CD28, sFv anti-CD28, CD30, LIGHT, OX40L, CD40, 4-1BBL, GITRL, ICOSL, CD70, CD80, CD86, or interferon or
   wherein the costimulatory domain activates CD28, HVEM, OX40, CD40L, 4-1BB, GITR, ICOS or CD27,
   or wherein the cytokine is IL-2, IL-7, IL-12, IL-15 or IL-21 or wherein the cytokine activates a receptor for IL-2, IL-7, IL-12, IL-15 or IL-21.

2. The multimeric polypeptide of claim 1, wherein the HIV epitope is a GAG epitope or a mutated GAG epitope.

3. The multimeric polypeptide of claim 1, wherein the multimeric polypeptide comprises:
   a) a first polypeptide comprising, in order from N-terminus to C-terminus:
      i) an epitope;
      ii) a first MHC polypeptide; and
      iii) one or more costimulatory domains; and b) a second polypeptide comprising, in order from N-terminus to C-terminus:
   i) a second MHC polypeptide; and
   ii) an Ig Fc polypeptide.

4. The multimeric polypeptide of claim 1, wherein the multimeric polypeptide comprises:
   I) a) a first polypeptide comprising, in order from N-terminus to C-terminus:
      i) an epitope; and
      ii) a first MHC polypeptide; and
   b) a second polypeptide comprising, in order from N-terminus to C-terminus:
      i) one or more costimulatory domains;
      ii) a second MHC polypeptide; and
      iii) an immunoglobulin (Ig) Fc polypeptide; or
   II) a) a first polypeptide comprising, in order from N-terminus to C-terminus:
      i) an epitope; and
      ii) a first MHC polypeptide; and
   b) a second polypeptide comprising, in order from N-terminus to C-terminus:
      i) a second MHC polypeptide; and
      ii) an Ig Fc polypeptide; and
      iii) one or more costimulatory domains; or
   III) a) a first polypeptide comprising, in order from N-terminus to C-terminus:
      i) an epitope; and
      ii) a first WIC polypeptide; and
   b) a second polypeptide comprising, in order from N-terminus to C-terminus:
      i) a second WIC polypeptide; and
      ii) one or more costimulatory domains; or
   IV) a) a first polypeptide comprising, in order from N-terminus to C-terminus:
      i) an epitope; and
      ii) a first WIC polypeptide; and
   b) a second polypeptide comprising, in order from N-terminus to C-terminus:
      i) one or more costimulatory domains; and
      ii) a second WIC polypeptide; or
   V) a) a first polypeptide comprising, in order from N-terminus to C-terminus:
      i) an epitope;
      ii) a first WIC polypeptide; and
      iii) one or more costimulatory domains; and
   b) a second polypeptide comprising, in order from N-terminus to C-terminus:
      i) a second WIC polypeptide.

5. The multimeric polypeptide of claim 1, wherein the non-Ig scaffold is an XTEN polypeptide, a transferrin polypeptide, an Fc receptor polypeptide, an elastin-like polypeptide, a silk-like polypeptide, or a silk-elastin-like polypeptide.

6. The multimeric polypeptide of claim 1, wherein the HIV epitope comprises the amino acid sequence SLYNTVATL, SLFNTVATL, SLFNTIATL, SLFNTVAVL, SLYNTIATL, SLYNTVAVL, SLYNTIAVL, SLFNTVATL, SLFNAVATL, SLFNAVAVL or SLFNTIAVL (SEQ ID NOS. 1-11, respectively).

7. The multimeric polypeptide of claim 1, comprising a first linker interposed between the epitope and the first WIC polypeptide.

8. The multimeric polypeptide of claim 7, wherein the first linker comprises a sequence -GCGAS-(GGGS)$_4$- (SEQ ID NO. 14).

9. The multimeric polypeptide of claim 1, comprising 2 or more a costimulatory domain polypeptides.

10. A nucleic acid comprising a nucleotide sequence encoding a recombinant polypeptide,
   i) wherein the recombinant polypeptide comprises, in order from N-terminus to C-terminus:
      (1) an HIV epitope;
      (2) a first major histocompatibility complex (MHC) polypeptide;
      (3) one or more costimulatory domain polypeptides and/or cytokine(s);
      (4) a proteolytically cleavable linker or a ribosome skipping signal;
      (5) a second MHC polypeptide; and
      (6) an immunoglobulin (Ig) Fc polypeptide;
         wherein the N-terminus of the first MHC polypeptide and the N-terminus of the second MHC polypeptide are covalently linked; or
   ii) wherein the recombinant polypeptide comprises, in order from N-terminus to C-terminus:
      (1) an HIV epitope;
      (2) a first MHC polypeptide;
      (3) a proteolytically cleavable linker or a ribosome skipping signal;
      (4) one or more costimulatory domain polypeptides and/or cytokine(s);
      (5) a second MHC polypeptide; and
      (6) an Ig Fc polypeptide;
         wherein the N-terminus of the first MHC polypeptide and the N-terminus of the second MHC polypeptide are covalently linked;
   and wherein the costimulatory domain is a GITRL, 4-1BBL, anti-CD28, sFv anti-CD28, CD30, LIGHT, OX40L, CD40, 4-1BBL, GITRL, ICOSL, CD70, CD80, CD86, or interferon or wherein the costimulatory domain activates CD28, HVEM, OX40, CD40L, 4-1BB, GITR, ICOS or CD27,
   or wherein the cytokine is IL-2, IL-7, IL-12, IL-15 or IL-21 or wherein the cytokine activates a receptor for IL-2, IL-7, IL-12, IL-15 or IL-21.

11. A recombinant expression vector comprising the nucleic acid of claim 10.

12. A host cell genetically modified with the recombinant expression vector of claim 11.

13. A composition comprising:
   I) a) a first nucleic acid comprising a nucleotide sequence encoding a first polypeptide comprising, in order from N-terminus to C-terminus:
      i) an HIV epitope;
      ii) a first MHC polypeptide; and
      iii) one or more costimulatory domain polypeptides and/or cytokine(s); and
   b) a first nucleic acid comprising a nucleotide sequence encoding a second polypeptide comprising, in order from N-terminus to C-terminus:
      i) a second MHC polypeptide; and
      ii) an Ig Fc polypeptide;
      wherein the N-terminus of the first MHC polypeptide and the N-terminus of the second MHC polypeptide are covalently linked;
      and wherein the costimulatory domain is a GITRL, 4-1BBL, anti-CD28, sFv anti-CD28, CD30, LIGHT, OX40L, CD40, 4-1BBL, GITRL, ICOSL, CD70, CD80, CD86, or interferon or
      wherein the costimulatory domain activates CD28, HVEM, OX40, CD40L, 4-1BB, GITR, ICOS or CD27,
      or wherein the cytokine is IL-2, IL-7, IL-12, IL-15 or IL-21 or wherein the cytokine activates a receptor for IL-2, IL-7, IL-12, IL-15 or IL-21; or II) a) a first nucleic acid comprising a nucleotide sequence encoding a first polypeptide comprising, in order from N-terminus to C-terminus:
   iii) an HIV epitope; and
   iv) a first MHC polypeptide; and
b) a first nucleic acid comprising a nucleotide sequence encoding a second polypeptide comprising, in order from N-terminus to C-terminus:
   i) one or more costimulatory domain polypeptides and/or cytokine(s);
   ii) a second MHC polypeptide; and
   iii) an Ig Fc polypeptide;
wherein the N-terminus of the first MHC polypeptide and the N-terminus of the second MHC polypeptide are covalently linked;
and wherein the costimulatory domain is a GITRL, 4-1BBL, anti-CD28, sFv anti-CD28, CD30, LIGHT, OX40L, CD40, 4-1BBL, GITRL, ICOSL, CD70, CD80, CD86, or interferon or
wherein the costimulatory domain activates CD28, HVEM, OX40, CD40L, 4-1BB, GITR, ICOS or CD27,
or wherein the cytokine is IL-2, IL-7, IL-12, IL-15 or IL-21 or wherein the cytokine activates a receptor for IL-2, IL-7, IL-12, IL-15 or IL-21.

14. A method of producing a multimeric polypeptide, the method comprising:
a) culturing the host cell of claim 12 in vitro in a culture medium under conditions such that the host cell synthesizes the multimeric polypeptide; and
b) isolating the multimeric polypeptide from the host cell and/or from the culture medium.

15. A method of selectively modulating the activity of an HIV epitope-specific T cell, the method comprising contacting the T cell with one or more of a first multimeric polypeptide of claim 1, wherein said contacting selectively modulates the activity of the HIV epitope-specific T cell.

16. A method of selectively modulating the activity of an HIV epitope-specific T cell in an individual, the method comprising administering to the individual an effective amount of the multimeric polypeptide of claim 1 effective to selectively modulate the activity of an HIV epitope-specific T cell in an individual.

17. A method of treating an HIV infection in an individual, the method comprising administering to the individual an amount of
a) the multimeric polypeptide of claim 1; or
b) one or more recombinant expression vectors comprising nucleotide sequences encoding the multimeric polypeptide of a); or
c) one or more mRNAs comprising nucleotide sequences encoding the multimeric polypeptide of a),
effective to modulate activity of HIV epitope-specific T cell in an individual.

18. A method of treating an HIV infection in an individual, the method comprising administering to the individual an amount of a) a plurality of multimeric polypeptides of claim 1, wherein at least two of the plurality of multimeric polypeptides comprise different HIV epitope sequences, or
b) one or more recombinant expression vectors comprising nucleotide sequences encoding a plurality of multimeric polypeptides of a), wherein at least two of the plurality of multimeric polypeptides comprise different HIV epitope sequences; or
c) one or more mRNAs comprising nucleotide sequences encoding a plurality of multimeric polypeptides of a), wherein at least two of the plurality of multimeric polypeptides comprise different HIV epitope sequences,
effective to modulate activity of HIV epitope-specific T cell in an individual.

19. A method of reactivating a latent HIV infected T-cell in an individual, the method comprising administering to the individual an amount of a multimeric polypeptide of claim 1, wherein at least one of the first and second MHC polypeptides is HLA-mismatched with the individual, effective to reactivate a latent HIV infected T-cell in an individual.

20. A method of treating a cytomegalovirus (CMV) infection in an individual, the method comprising administering to the individual an amount of:
a) one or more multimeric polypeptides of claim 1 comprising a CMV epitope, or
b) one or more recombinant expression vectors comprising nucleotide sequences encoding a such multimeric polypeptides as described herein comprising a CMV epitope; or
c) one or more mRNAs comprising nucleotide sequences encoding multimeric polypeptides as described herein comprising a CMV epitope,
effective to modulate activity of CMV epitope-specific T cell in an individual.

21. A multimeric polypeptide of claim 1, wherein the N-terminus of the first MHC polypeptide and the N-terminus of the second MHC polypeptide are covalently linked via a disulfide bond.

22. A multimeric polypeptide of claim 10, wherein the N-terminus of the first MHC polypeptide and the N-terminus of the second MHC polypeptide are covalently linked via a disulfide bond.

23. A multimeric polypeptide of claim 13, wherein the N-terminus of the first MHC polypeptide and the N-terminus of the second MHC polypeptide are covalently linked via a disulfide bond.

24. The method of claim 19, wherein the at least one first and second MHC polypeptide HLA-mismatched with the individual, is allogeneic to the individual.

* * * * *

SEQUENCE LISTING

```
<160> NUMBER OF SEQ ID NOS: 21

<210> SEQ ID NO 1
<211> LENGTH: 9
<212> TYPE: PRT
<213> ORGANISM: Human immunodeficiency virus

<400> SEQUENCE: 1

Ser Leu Tyr Asn Thr Val Ala Thr Leu
1               5

<210> SEQ ID NO 2
<211> LENGTH: 9
<212> TYPE: PRT
<213> ORGANISM: Human immunodeficiency virus

<400> SEQUENCE: 2

Ser Leu Phe Asn Thr Val Ala Thr Leu
1               5

<210> SEQ ID NO 3
<211> LENGTH: 9
<212> TYPE: PRT
<213> ORGANISM: Human immunodeficiency virus

<400> SEQUENCE: 3

Ser Leu Phe Asn Thr Ile Ala Thr Leu
1               5

<210> SEQ ID NO 4
<211> LENGTH: 9
<212> TYPE: PRT
<213> ORGANISM: Human immunodeficiency virus

<400> SEQUENCE: 4

Ser Leu Phe Asn Thr Val Ala Val Leu
1               5

<210> SEQ ID NO 5
<211> LENGTH: 9
<212> TYPE: PRT
<213> ORGANISM: Human immunodeficiency virus

<400> SEQUENCE: 5

Ser Leu Tyr Asn Thr Ile Ala Thr Leu
1               5
```

```
<210> SEQ ID NO 6
<211> LENGTH: 9
<212> TYPE: PRT
<213> ORGANISM: Human immunodeficiency virus

<400> SEQUENCE: 6

Ser Leu Tyr Asn Thr Val Ala Val Leu
1               5

<210> SEQ ID NO 7
<211> LENGTH: 9
<212> TYPE: PRT
<213> ORGANISM: Human immunodeficiency virus

<400> SEQUENCE: 7

Ser Leu Tyr Asn Thr Ile Ala Val Leu
1               5

<210> SEQ ID NO 8
<211> LENGTH: 9
<212> TYPE: PRT
<213> ORGANISM: Human immunodeficiency virus

<400> SEQUENCE: 8

Ser Leu Phe Asn Thr Val Ala Thr Leu
1               5

<210> SEQ ID NO 9
<211> LENGTH: 9
<212> TYPE: PRT
<213> ORGANISM: Human immunodeficiency virus

<400> SEQUENCE: 9

Ser Leu Phe Asn Ala Val Ala Thr Leu
1               5

<210> SEQ ID NO 10
<211> LENGTH: 9
<212> TYPE: PRT
<213> ORGANISM: Human immunodeficiency virus

<400> SEQUENCE: 10

Ser Leu Phe Asn Ala Val Ala Val Leu
1               5

<210> SEQ ID NO 11
<211> LENGTH: 9
<212> TYPE: PRT
<213> ORGANISM: Human immunodeficiency virus

<400> SEQUENCE: 11

Ser Leu Phe Asn Thr Ile Ala Val Leu
1               5

<210> SEQ ID NO 12
<211> LENGTH: 5
<212> TYPE: PRT
<213> ORGANISM: Artificial Sequence
<220> FEATURE:
<223> OTHER INFORMATION: chemically synthesized

<400> SEQUENCE: 12

Gly Gly Gly Gly Ser
1               5
```

```
<210> SEQ ID NO 13
<211> LENGTH: 5
<212> TYPE: PRT
<213> ORGANISM: Artificial Sequence
<220> FEATURE:
<223> OTHER INFORMATION: chemically synthesized

<400> SEQUENCE: 13

Gly Cys Gly Ala Ser
1               5

<210> SEQ ID NO 14
<211> LENGTH: 5
<212> TYPE: PRT
<213> ORGANISM: Artificial Sequence
<220> FEATURE:
<223> OTHER INFORMATION: chemically synthesized

<400> SEQUENCE: 14

Gly Cys Gly Ala Ser
1               5

<210> SEQ ID NO 15
<211> LENGTH: 8
<212> TYPE: PRT
<213> ORGANISM: Artificial Sequence
<220> FEATURE:
<223> OTHER INFORMATION: chemically synthesized

<400> SEQUENCE: 15

Leu Glu Val Leu Phe Gln Gly Pro
1               5

<210> SEQ ID NO 16
<211> LENGTH: 7
<212> TYPE: PRT
<213> ORGANISM: Artificial Sequence
<220> FEATURE:
<223> OTHER INFORMATION: chemically synthesized

<400> SEQUENCE: 16

Glu Asn Leu Tyr Thr Gln Ser
1               5

<210> SEQ ID NO 17
<211> LENGTH: 4
<212> TYPE: PRT
<213> ORGANISM: Artificial Sequence
<220> FEATURE:
<223> OTHER INFORMATION: chemically synthesized

<400> SEQUENCE: 17

Leu Val Pro Arg
1

<210> SEQ ID NO 18
<211> LENGTH: 22
<212> TYPE: PRT
<213> ORGANISM: Artificial Sequence
<220> FEATURE:
<223> OTHER INFORMATION: chemically synthesized

<400> SEQUENCE: 18

Gly Ser Gly Ala Thr Asn Phe Ser Leu Leu Lys Gln Ala Gly Asp Val
1               5                   10                  15
```

```
Glu Glu Asn Pro Gly Pro
            20

<210> SEQ ID NO 19
<211> LENGTH: 21
<212> TYPE: PRT
<213> ORGANISM: Artificial Sequence
<220> FEATURE:
<223> OTHER INFORMATION: chemically synthesized

<400> SEQUENCE: 19

Gly Ser Gly Glu Gly Arg Gly Ser Leu Leu Thr Cys Gly Asp Val Glu
1               5                   10                  15

Glu Asn Pro Gly Pro
            20

<210> SEQ ID NO 20
<211> LENGTH: 23
<212> TYPE: PRT
<213> ORGANISM: Artificial Sequence
<220> FEATURE:
<223> OTHER INFORMATION: chemically synthesized

<400> SEQUENCE: 20

Gly Ser Gly Gln Cys Thr Asn Tyr Ala Leu Leu Lys Leu Ala Gly Asp
1               5                   10                  15

Val Glu Ser Asn Pro Gly Pro
            20

<210> SEQ ID NO 21
<211> LENGTH: 25
<212> TYPE: PRT
<213> ORGANISM: Artificial Sequence
<220> FEATURE:
<223> OTHER INFORMATION: chemically synthesized

<400> SEQUENCE: 21

Gly Ser Gly Val Lys Gln Thr Leu Asn Phe Asp Leu Leu Lys Leu Ala
1               5                   10                  15

Gly Asp Val Glu Ser Asn Pro Gly Pro
            20                  25
```